(12) United States Patent
Spender et al.

(10) Patent No.: US 11,530,517 B2
(45) Date of Patent: Dec. 20, 2022

(54) SACCHARIDE FATTY ACID ESTER INORGANIC PARTICLE COMBINATIONS

(71) Applicant: GREENTECH GLOBAL PTE. LTD., Singapore (SG)

(72) Inventors: Jonathan Spender, Enfield, ME (US); Michael Albert Bilodeau, Brewer, ME (US); Samuel Mikail, Kew Gardens, NY (US)

(73) Assignee: GREENTECH GLOBAL PTE. LTD., Singapore (SG)

( * ) Notice: Subject to any disclaimer, the term of this patent is extended or adjusted under 35 U.S.C. 154(b) by 0 days.

(21) Appl. No.: 16/456,433

(22) Filed: Jun. 28, 2019

(65) Prior Publication Data
US 2019/0323177 A1 Oct. 24, 2019

Related U.S. Application Data

(63) Continuation-in-part of application No. 15/693,186, filed on Aug. 31, 2017, now Pat. No. 10,730,959.

(60) Provisional application No. 62/722,910, filed on Aug. 26, 2018, provisional application No. 62/382,690, filed on Sep. 1, 2016, provisional application No. 62/432,133, filed on Dec. 9, 2016, provisional application No. 62/468,229, filed on Mar. 7, 2017.

(51) Int. Cl.
| | |
|---|---|
| *D21H 21/16* | (2006.01) |
| *C07H 13/06* | (2006.01) |
| *D21H 17/14* | (2006.01) |
| *D21H 17/26* | (2006.01) |
| *D21H 17/28* | (2006.01) |
| *D21H 19/54* | (2006.01) |
| *D21H 17/67* | (2006.01) |
| *D21H 19/46* | (2006.01) |
| *D21H 19/40* | (2006.01) |
| *D21H 19/38* | (2006.01) |
| *D21H 19/52* | (2006.01) |
| *D21H 17/68* | (2006.01) |

(52) U.S. Cl.
CPC ............ *D21H 21/16* (2013.01); *C07H 13/06* (2013.01); *D21H 17/14* (2013.01); *D21H 17/26* (2013.01); *D21H 17/28* (2013.01); *D21H 17/675* (2013.01); *D21H 17/68* (2013.01); *D21H 19/385* (2013.01); *D21H 19/40* (2013.01); *D21H 19/46* (2013.01); *D21H 19/52* (2013.01); *D21H 19/54* (2013.01)

(58) Field of Classification Search
CPC .............................. D21H 11/00; D21H 13/00
See application file for complete search history.

(56) References Cited

U.S. PATENT DOCUMENTS

| | | | | |
|---|---|---|---|---|
| 2007/0036847 | A1* | 2/2007 | Yoshinaga | ........... A61K 9/7053 |
| | | | | 424/448 |
| 2014/0363581 | A1* | 12/2014 | Nagoshi | ................ D21H 17/74 |
| | | | | 427/427.7 |

FOREIGN PATENT DOCUMENTS

| | | | | |
|---|---|---|---|---|
| CN | 104263206 A | * | 1/2015 | |
| JP | 52055708 A | * | 7/1990 | |

OTHER PUBLICATIONS

Uchiyama JP 52055708 A, Machine Translation. (Year: 1977).*

* cited by examiner

*Primary Examiner* — Leigh C Maier
*Assistant Examiner* — Everett White
(74) *Attorney, Agent, or Firm* — Sughrue Mion, PLLC

(57) ABSTRACT

The present disclosure describes methods of treating cellulosic materials with compositions that allow greater retention of inorganic particles on cellulosic substrates. The methods as disclosed provide combining saccharide fatty acid esters (SFAE) with such inorganic particles and applying such combinations on cellulosic materials to eliminate or reduce the use of retention aids or binders for filler in the paper making process. Compositions comprising such combinations of SFAE and inorganic particles are also disclosed.

22 Claims, 5 Drawing Sheets

SACCHARIDE FATTY ACID ESTER INORGANIC PARTICLE COMBINATIONS

CROSS REFERENCE TO RELATED APPLICATIONS

This application is a continuation-in-part of U.S. application Ser. No. 15/693,186, filed Aug. 31, 2017(now U.S. Pat. No. 10,730,959), which claims benefit under 35 U.S.C. § 119(e) to U.S. Provisional Application Nos. 62/382,690, filed Sep. 1, 2016; 62/432,133, filed Dec. 9, 2016; and 62/468,229, filed Mar. 7, 2017; and this application claims benefit under 35 U.S.C. § 119(e) to U.S. Provisional Application No. 62/722,910, filed Aug. 26, 2018, which is incorporated by reference herein in its entirety.

BACKGROUND OF THE INVENTION

Field of the Invention

The present invention relates generally to treating cellulosic-based materials, and more specifically to treating such materials with saccharide fatty acid esters (SFAE) in combination with inorganic particles, including compositions containing such combinations.

Background Information

Inorganic particles, such as kaolin, talc, calcium carbonate, and $TiO_2$, are typically used in paper making processes as filler. Calcium carbonate, for example, is used in paper mills as a filler material in the alkaline papermaking process. Presently, calcium carbonate dominates over other papermaking filler materials (e.g., kaolin). The main reason behind the preference for calcium carbonate is the demand for brighter and bulkier paper. There are significant benefits to the use of calcium carbonate in the alkaline papermaking process (e.g., calcium carbonate is cheaper and it has high brightness, creates a porous surface on the paper sheet, improves printability, lowers binder demand, increases machine speed and productivity, improves water drainage, improves machine runnability, is cost-effective in papermaking processes, it can reduce fiber consumption, and can obtain more retention compared to other paper fillers).

Usually calcium carbonate occurs in three natural forms such as limestone, chalk and marble. Naturally, it forms between the reactions of calcium salt and carbon dioxide. There are two types of calcium carbonate used in paper mills: ground calcium carbonate (GCC) and precipitated calcium carbonate (PCC).

Ground calcium carbonate is manufactured by grinding limestone or marble and finds use because of its high brightness and purity. Generally, the particle shape of ground calcium carbonate is rhombohedral. This filler material is used in alkaline, wood free papermaking processes. The brightness of GCC is about 86-95%.

The rough particle shape and small amounts of quartz often found in GCC create a problem; it is more abrasive and shortens the life of paper machine forming wires and press felts.

Precipitated calcium carbonate is the form of $CaCO_3$ which is manufactured by chemical reactions and the process is known as the carbonation process. PCC improves the drawback of GCC, it provides better gloss and opacity properties for the paper. The structure of PCC is different from the structure of GCC. The crystal structure of PCC can be controlled and includes needle-shaped, rhombohedral (cubic), scalenohedral (triangular) and prismatic. The brightness of PCC is about 90-97%. However, PCC containing paper sheets can have poorer formation than GCC containing paper sheets.

On modern high-speed, twin-wire paper machines, the turbulence needed to obtain good formation often causes low retention of fillers. In addition, for both types of calcium carbonates, they have no adhesion on their own to cellulose, and require a retention aid or binder to attach to pulp. Typically, such retention aids or binders include papermaker's alum, synthetic polymers, polyacrylamides, microparticle systems, latex, starch, and polyvinyl alcohol (PvOH), which retention aids or binders can increase costs, or make products less "green" (e.g., synthetic polymers) where desired.

It would be desirable to bind calcium carbonates to make use of retention aids or binders unnecessary or reduce the amount of retention aid or binder needed to attach inorganic particles to cellulosic surfaces.

SUMMARY OF THE INVENTION

The present disclosure relates to methods of treating cellulosic materials with a composition that allows, inter alia, greater retention of inorganic particles (i.e., fillers). The methods as disclosed provide combining saccharide fatty acid esters (SFAE) with such fillers and applying such combinations on cellulose to eliminate or reduce the use of retention aids or binders for filler in the paper making process. Compositions comprising combinations of SFAE and inorganic particles are also disclosed.

In embodiments, a composition comprising a saccharide fatty acid ester (SFAE) and inorganic particles is disclosed, where the SFAE is present at a sufficient concentration to cause the inorganic particles to be retained on the cellulose-based material, and where the substrate containing the composition exhibits greater water resistance and/or grease resistance compared to a substrate containing the composition comprising the inorganic particles or one or more SFAE alone.

In one aspect, the SFAE include all unsaturated fatty acids, all saturated fatty acids or a mixture of saturated and unsaturated fatty acids, and optionally, further includes one or more binders selected from PvOH or starch.

In another aspect, the SFAE is a mixture of two or more different SFAEs, where the two or more different SFAE contain all saturated fatty acids.

In one aspect, the inorganic particles include clay, ground calcium carbonate, precipitated calcium carbonate, talc, titanium dioxide and combinations thereof, and where the inorganic particles comprise at least 1% of the composition on a dry basis (db).

In another aspect, the SFAE contains at least one saccharide and at least one aliphatic group comprising 8 to 30 carbons. In one aspect, the inorganic particle is calcium carbonate, where the substrate exhibits water resistance. In a related aspect, the inorganic particle is clay, where the substrate exhibits grease resistance.

In one aspect, the cellulose based substrate includes paper, paperboard, paper pulp, a food storage carton, a food storage bag, a shipping bag, a coffee or tea container, a tea bag, bacon board, diapers, weed-block/barrier fabric or film, mulching film, plant pots, packing beads, bubble wrap, oil absorbent material, laminates, envelops, gift cards, credit cards, gloves, raincoats, OGR paper, a shopping bag, a compost bag, release paper, eating utensil, a hot or cold beverage container, cup, paper towels, plate, a carbonated liquid storage bottle, insulating material, a non-carbonated liquid storage bottle, wrapping food film, a garbage disposal container, a food handling implement, a cup lid, a screw on cup lid of moldable paper, paper straws, a fabric fibre, a water storage and conveying implement, medical use paperboard, release paper, an alcoholic or non-alcoholic drink storage and conveying implement, casing, an electronic good outer screen, an internal or external piece of furniture, a curtain, upholstery, film, box, sheet, tray, pipe, water conduit, pharmaceutical product packaging, clothing, medical device, contraceptive, camping equipment, molded cellulosic fiber material and combinations thereof.

In embodiments, an article of manufacture is disclosed including a coating containing one or more saccharide fatty acid esters (SFAE), inorganic particles, a cellulose based substrate, and optionally, one or more binders, where the inorganic particles are present in the coating at a concentration of at least 1% on a dry basis (db). In a related aspect, the cellulose based substrate includes paper, paperboard, paper pulp, a food storage carton, a food storage bag, a shipping bag, a coffee or tea container, a tea bag, bacon board, diapers, weed-block/barrier fabric or film, mulching film, plant pots, packing beads, bubble wrap, oil absorbent material, laminates, envelops, gift cards, credit cards, gloves, raincoats, OGR paper, a shopping bag, a compost bag, release paper, eating utensil, a hot or cold beverage container, cup, paper towels, plate, a carbonated liquid storage bottle, insulating material, a non-carbonated liquid storage bottle, wrapping food film, a garbage disposal container, a food handling implement, a cup lid, a screw on cup lid of moldable paper, paper straws, a fabric fibre, a water storage and conveying implement, medical use paperboard, release paper, an alcoholic or non-alcoholic drink storage and conveying implement, casing, an electronic good outer screen, an internal or external piece of furniture, a curtain, upholstery, film, box, sheet, tray, pipe, water conduit, pharmaceutical product packaging, clothing, medical device, contraceptive, camping equipment, molded cellulosic fiber material and combinations thereof.

In embodiments, a method of treating a cellulosic substrate is disclosed including adding at least one saccharide fatty acid ester (SFAE) to a composition comprising inorganic particles to form a mixture; applying said mixture to at least one surface of said cellulosic substrate; and curing for a sufficient time to allow the mixture to adhere to the at least one surface, where the cured surface exhibits higher hydrophobicity and/or lipophobicity compared to a surface treated with the at least one SFAE or the composition comprising the inorganic particles alone.

In one aspect, the treated cellulosic surface is hydrophobic. In another aspect, the treated cellulosic surface is lipophobic.

In one aspect, the SFAE includes all saturated fatty acids or a mixture of saturated and unsaturated fatty acids. In another aspect, the SFAE is a mixture of two or more different SFAEs.

In one aspect, the inorganic particles include clay, ground calcium carbonate, precipitated calcium carbonate, talc, titanium dioxide and combinations thereof, where the inorganic particles are present in the mixture at a concentration of at least about 1% on a dry basis (db). In a related aspect, the composition further comprises polyvinyl alcohol or starch.

In one aspect, the inorganic particles include calcium carbonate, where the calcium carbonate comprises greater than or equal to about 50% of the mixture on a dry basis (db).

In another aspect, the cellulosic substrate includes paper, paperboard, paper pulp, a carton for food storage, a bag for food storage, a shipping bag, a container for coffee or tea, a tea bag, bacon board, diapers, weed-block/barrier fabric or film, mulching film, plant pots, packing beads, bubble wrap, oil absorbent material, laminates, envelops, gift cards, credit cards, gloves, raincoats, OGR paper, a shopping bag, a compost bag, release paper, eating utensil, container for holding hot or cold beverages, cup, paper towels, plate, a bottle for carbonated liquid storage, insulating material, a bottle for non-carbonated liquid storage, film for wrapping food, a garbage disposal container, a food handling implement, a lid for a cup, a screw on cup lid of moldable paper, paper straws, a fabric fibre, a water storage and conveying implement, medical use paperboard, release paper, a storage and conveying implement for alcoholic or non-alcoholic drinks, an outer casing or screen for electronic goods, an internal or external piece of furniture, a curtain, upholstery, film, box, sheet, tray, pipe, water conduit, packaging for pharmaceutical products, clothing, medical device, contraceptive, camping equipment, cellulosic material that is molded and combinations thereof

DETAILED DESCRIPTION OF THE INVENTION

Figure 1:
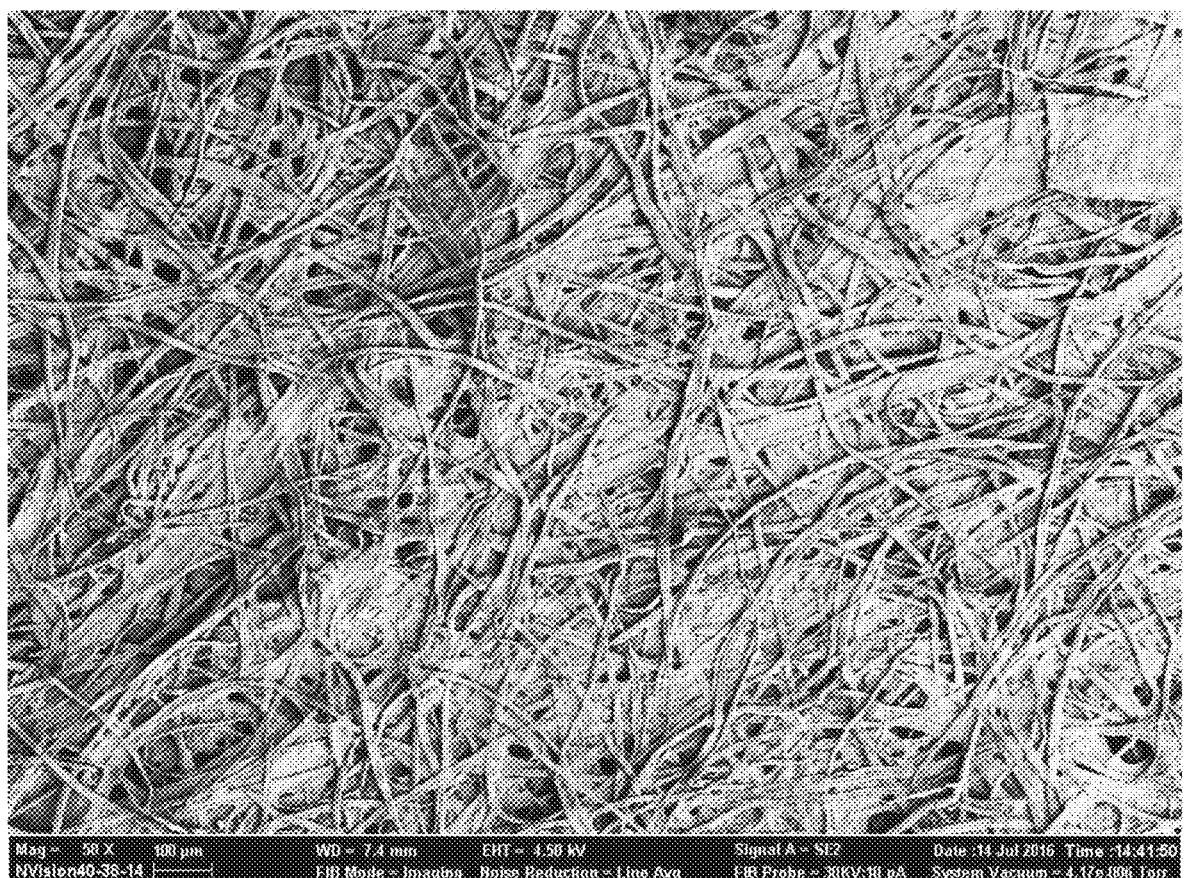
FIG. 1 shows a scanning electron micrograph (SEM) of untreated, medium porosity Whatman Filter Paper (58× magnification).

Before the present composition, methods, and methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "a saccharide fatty acid ester" includes one or more saccharide fatty acid esters, and/or compositions of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein may be used in the practice or testing of the invention, as it will be understood that modifications and variations are encompassed within the spirit and scope of the instant disclosure.

As used herein, "about," "approximately," "substantially" and "significantly" will be understood by a person of ordinary skill in the art and will vary in some extent depending on the context in which they are used. If there are uses of the term which are not clear to persons of ordinary skill in the art given the context in which it is used, "about" and "approximately" will mean plus or minus <10% of particular term and "substantially" and "significantly" will mean plus or minus >10% of the particular term. "Comprising" and "consisting essentially of" have their customary meaning in the art.

All pigments must be uniformly retained in the sheet to be effective. Paper can be made cheaper when using fillers that are less costly than fibers. However, the proportion of filler in the sheet is limited by the resultant reduction in strength, bulk and sizing quality. While the trend is definitely toward higher filler contents, once the pigment concentration is above 10 or 20% in any barrier coating, barrier properties are significantly reduced.

Although not a polymer, per se, SFAEs aid in retention of filler or inorganic particles such as PCC. While not being bound by theory, the SFAEs may crosslink or provide a network with surfaces on the fines and fibers. The combination performs well and allows a higher level of attachment without compromising product quality, including providing an increased level of performance.

Also, organic particles such as uncooked starch, particles of wood, oat hulls and the like offer bulk and caliper which are greatly needed in some products may be added, whereas the inorganics increase density. Further, for hydrophobic polymers that might create unwanted particles and/or sticky masses or deposits, including wood resin, hot melt waxes, bioplastics and the like, the use of SFAE-inorganic particle combinations may overcome such unwanted agglomerations.

Moreover, the addition of a composition comprising a mixture of inorganic particles and SFAEs would offer the improvement of fine tuning of the various properties of a sheet. For example, such sheets may contain wood fiber, and include a bioplastic fiber along with SFAE combinations to waterproof such a sheet. The combinations as envisaged would allow the use of cheaper, more common materials, such as mechanical or recycled pulp to be a larger percentage of the mass of the sheet. In such a case, the addition of, for example, a calcium carbonate-SFAE mixture would offer the improvement of allowing the control of the density of the sheet.

In embodiments, the present disclosure shows that by treating the cellulosic materials with a combination of inorganic particles and saccharide fatty acid esters the resulting material, inter alia, can be made strongly hydrophobic and/or lipophobic. In addition, these saccharide fatty acid esters, for example, once removed by bacterial enzymes, are easily digested as such. The derivatized surface displays a great deal of heat resistance, being able to withstand temperatures as high as 250° C. and may be more impermeant to gases than the base substrate underneath. The material is therefore an ideal solution to the problem of derivatizing the hydrophilic surface of cellulose, in any embodiment in which cellulose materials may be employed.

Advantages of the products and methods as disclosed herein include that the coating composition is made from renewable agricultural resources—saccharides and vegetable oils; is biodegradable; has a low toxicity profile and suitable for food contact; can be tuned to reduce the coefficient of friction of the paper/paperboard surface (i.e., does not make the paper too slippery for downstream processing or end use), even at high levels of water resistance; may or may not be used with special emulsification equipment or emulsification agents; and is compatible with traditional paper recycling programs: i.e., poses no adverse impact on recycling operations, like polyethylene, polylactic acid, or wax coated papers do. Further, the extended use of inorganics, such as PCC, takes advantage of the inherent property of the filler (e.g., less abrasive).

As used herein, "biobased" means a material intentionally made from substances derived from living (or once-living) organisms. In a related aspect, material containing at least about 50% of such substances is considered biobased.

As used herein, "bind", including grammatical variations thereof, means to cohere or cause to cohere essentially as a single mass.

As used herein, "cellulosic" means natural, synthetic or semisynthetic materials that can be molded or extruded into objects (e.g., bags, sheets) or films or filaments, which may be used for making such objects or films or filaments, that is structurally and functionally similar to cellulose, e.g., coatings and adhesives (e.g., carboxymethylcellulose). In another example, cellulose, a complex carbohydrate $(C_6H_{10}O_5)_n$ that is composed of glucose units, which forms the main constituent of the cell wall in most plants, is cellulosic.

As used herein, "coating weight" is the weight of a material (wet or dry) applied to a substrate. It is expressed in pounds per specified ream or grams per square meter.

As used herein, "compostable" means these solid products are biodegradable into the soil.

As used herein, "dry basis" is the measure of the mass of all constituents excluding water (e.g., solids).

As used herein, "edge wicking" means the sorption of water in a paper structure at the outside limit of said structure by one or more mechanisms including, but not limited to, capillary penetration in the pores between fibers, diffusion through fibers and bonds, and surface diffusion on the fibers. In a related aspect, the saccharide fatty acid ester containing coating as described herein prevents edge wicking in treated products. In one aspect, a similar problem exists with grease/oil entering creases that may be present in paper or paper products. Such a "grease creasing effect" may be defined as the sorption of grease in a paper structure that is created by folding, pressing or crushing said paper structure.

As used herein, "effect", including grammatical variations thereof, means to impart a particular property to a specific material.

As used herein, "hydrophobe" means a substance that does not attract water. For example, waxes, rosins, resins, saccharide fatty acid esters, diketenes, shellacs, vinyl acetates, PLA, PEI, oils, fats, lipids, other water repellant chemicals or combinations thereof are hydrophobes.

As used herein, "hydrophobicity" means the property of being water-repellent, tending to repel and not absorb water.

As used herein, "lipid resistance" or "lipophobicity" means the property of being lipid-repellent, tending to repel and not absorb lipids, grease, fats and the like. In a related aspect, the grease resistance may be measured by a "3M KIT" test or a TAPPI T559 Kit test.

As used herein, "cellulose-containing material" or "cellulose-based material" means a composition which consists essentially of cellulose. For example, such material may include, but is not limited to, paper, paperboard, paper pulp, a carton for food storage, a bag for food storage, a shipping bag, a container for coffee or tea, a tea bag, bacon board, diapers, weed-block/barrier fabric or film, mulching film, plant pots, packing beads, bubble wrap, oil absorbent material, laminates, envelops, gift cards, credit cards, gloves, raincoats, OGR paper, a shopping bag, a compost bag, release paper, eating utensil, container for holding hot or cold beverages, cup, paper towels, plate, a bottle for carbonated liquid storage, insulating material, a bottle for non-carbonated liquid storage, film for wrapping food, a garbage disposal container, a food handling implement, a lid for a cup, paper straws, a fabric fibre, a water storage and conveying implement, paperboard from medical use, release paper, a storage and conveying implement for alcoholic or non-alcoholic drinks, an outer casing or screen for electronic goods, an internal or external piece of furniture, a curtain, upholstery, film, box, sheet, tray, pipe, water conduit, packaging for pharmaceutical products, clothing, medical device, contraceptive, camping equipment, cellulosic material that is molded and combinations thereof.

As used herein, "release paper" means a paper sheet used to prevent a sticky surface from prematurely adhering to an adhesive or a mastic. In one aspect, the coatings as disclosed herein can be used to replace or reduce the use of silicon or other coatings to produce a material having a low surface energy. Determining the surface energy may be readily achieved by measuring contact angle (e.g., Optical Tensiometer and/or High Pressure Chamber; Dyne Testing, Staffordshire, United Kingdom) or by use of Surface Energy Test Pens or Inks (see, e.g., Dyne Testing, Staffordshire, United Kingdom).

As used herein "releasable" with reference to the SFAE means that the SFAE coating, once applied, may be removed from the cellulose-based material (e.g., removeable by manipulating physical properties). As used herein "non-releasable" with reference to the SFAE means that the SFAE coating, once applied, is substantially irreversibly bound to the cellulose-based material (e.g., removable by chemical means).

As used herein, "fibers in solution" or "pulp" means a lignocellulosic fibrous material prepared by chemically or mechanically separating cellulose fibers from wood, fiber crops or waste paper. In a related aspect, where cellulose fibers are treated by the methods as disclosed herein, the cellulose fibers themselves contain bound saccharide fatty acid esters as isolated entities, and where the bound cellulose fibers have separate and distinct properties from free fibers (e.g., pulp- or cellulose fiber- or nanocellulose or microfibrillated cellulose-saccharide fatty acid ester bound material would not form hydrogen bonds between fibers as readily as unbound fibers).

As used herein, "repulpable" means to make a paper or paperboard product suitable for crushing into a soft, shapeless mass for reuse in the production of paper or paperboard.

As used herein, "tunable", including grammatical variations thereof, means to adjust or adapt a process to achieve a particular result.

As used herein, "water contact angle" means the angle measured through a liquid, where a liquid/vapor interface meets a solid surface. It quantifies the wettability of the solid surface by the liquid. The contact angle is a reflection of how strongly the liquid and solid molecules interact with each other, relative to how strongly each interacts with its own kind. On many highly hydrophilic surfaces, water droplets will exhibit contact angles of 0° to 30°. Generally, if the water contact angle is larger than 90°, the solid surface is considered hydrophobic. Water contact angle may be readily obtained using an Optical Tensiometer (see, e.g., Dyne Testing, Staffordshire, United Kingdom).

As used herein, "water vapour permeability" means breathability or a textile's ability to transfer moisture. There are at least two different measurement methods. One, the MVTR Test (Moisture Vapour Transmission Rate) in accordance with ISO 15496, describes the water vapor permeability (WVP) of a fabric and therefore the degree of perspiration transport to the outside air. The measurements determine how many grams of moisture (water vapor) pass through a square meter of fabric in 24 hours (the higher the level, the higher the breathability).

In one aspect, TAPPI T 530 Hercules size test (i.e., size test for paper by ink resistance) may be used to determine water resistance. Ink resistance by the Hercules method is best classified as a direct measurement test for the degree of penetration. Others classify it as a rate of penetration test. There is no one best test for "measuring sizing." Test selection depends on end use and mill control needs. This method is especially suitable for use as a mill control sizing test to accurately detect changes in sizing level. It offers the sensitivity of the ink float test while providing reproducible results, shorter test times, and automatic end point determination.

Sizing, as measured by resistance to permeation through or absorption into paper of aqueous liquids, is an important characteristic of many papers. Typical of these are bag, containerboard, butcher's wrap, writing, and some printing grades.

This method may be used to monitor paper or board production for specific end uses provided acceptable correlation has been established between test values and the paper's end use performance. Due to the nature of the test and the penetrant, it will not necessarily correlate sufficiently to be applicable to all end use requirements. This method measures sizing by rate of penetration. Other methods measure sizing by surface contact, surface penetration, or absorption. Size tests are selected based on the ability to simulate the means of water contact or absorption in end use. This method can also be used to optimize size chemical usage costs.

As used herein, "oxygen permeability" means the degree to which a polymer allows the passage of a gas or fluid. Oxygen permeability (Dk) of a material is a function of the diffusivity (D) (i.e., the speed at which oxygen molecules traverse the material) and the solubility (k) (or the amount of oxygen molecules absorbed, per volume, in the material). Values of oxygen permeability (Dk) typically fall within the range $10$-$150 \times 10^{-11}$ (cm$^2$ ml O$_2$)/(s ml mmHg). A semi-logarithmic relationship has been demonstrated between hydrogel water content and oxygen permeability (Unit: Barrer unit). The International Organization for Standardization (ISO) has specified permeability using the SI unit hectopascal (hPa) for pressure. Hence Dk=$10^{-11}$ (cm$^2$ ml O$_2$)/(s ml hPa). The Barrer unit can be converted to hPa unit by multiplying it by the constant 0.75.

As used herein "biodegradable", including grammatical variations thereof, means capable of being broken down especially into innocuous products by the action of living things (e.g., by microorganisms).

As used herein, "recyclable", including grammatical variations thereof, means a material that is treatable or that can be processed (with used and/or waste items) so as to make said material suitable for reuse.

As used herein, "filler" means finely divided white mineral (or pigments) added to paper making furnishes to improve the optical and physical properties of the sheet. The particles serve to fill in the spaces and crevices between the fibers, thus, producing a sheet with increased brightness, opacity, smoothness, gloss, and printability, but generally, lower bonding and tear strength. Common paper making fillers include clay (kaolin, bentonite), calcium carbonate (both GCC and PCC), talc (magnesium silicate), and titanium dioxide.

As used herein, "Gurley second" or "Gurley number" is a unit describing the number of seconds required for 100 cubic centimeters (deciliter) of air to pass through 1.0 square inch of a given material at a pressure differential of 4.88 inches of water (0.176 psi) (ISO 5636-5:2003)(Porosity). In addition, for stiffness, "Gurley number" is a unit for a piece of vertically held material measuring the force required to deflect said material a given amount (1 milligram of force). Such values may be measured on a Gurley Precision Instruments' device (Troy, N.Y.).

HLB—The hydrophilic-lipophilic balance of a surfactant is a measure of the degree to which it is hydrophilic or lipophilic, determined by calculating values for the different regions of the molecule.

Griffin's method for non-ionic surfactants as described in 1954 works as follows:

$$HLB=20*M_h/M$$

where $M_h$ is the molecular mass of the hydrophilic portion of the molecule, and M is the molecular mass of the whole molecule, giving a result on a scale of 0 to 20. An HLB value of 0 corresponds to a completely lipophilic/hydrophobic molecule, and a value of 20 corresponds to a completely hydrophilic/lipophobic molecule.

The HLB value can be used to predict the surfactant properties of a molecule:

<10: Lipid-soluble (water-insoluble)
>10: Water-soluble (lipid-insoluble)
1.5 to 3: anti-foaming agent
3 to 6: W/O (water in oil) emulsifier
7 to 9: wetting and spreading agent
13 to 15: detergent
12 to 16: O/W (oil in water) emulsifier
15 to 18: solubiliser or hydrotrope In some embodiments, the HLB values for the saccharide fatty acid esters (or composition comprising said ester) as disclosed herein may be in the lower range. In other embodiments, the HLB values for the saccharide fatty acid esters (or composition comprising said ester) as disclosed herein may be in the middle to higher ranges. In embodiments, mixing SFAEs with different HLB values may be used.

As used herein, "SEFOSE®" denotes a sucrose fatty acid ester made from soybean oil (soyate) which is commercially available from Procter & Gamble Chemicals (Cincinnati, Ohio) under the trade name SEFOSE 1618U (see sucrose polysoyate below), which contains one or more fatty acids that are unsaturated. As used herein, "OLEAN®" denotes a sucrose fatty acid ester which is available from Procter & Gamble Chemicals having the formula $C_{n+12}H_{2n+22}O_{13}$, where all fatty acids are saturated. In addition, SFAEs may be purchased from Mitsubishi Chemicals Foods Corporation (Tokyo, JP), which offers a variety of such SFAEs.

As used herein, "soyate" means a mixture of salts of fatty acids from soybean oil.

As used herein, "oilseed fatty acids" means fatty acids from plants, including but not limited to soybeans, peanuts, rapeseeds, barley, canola, sesame seeds, cottonseeds, palm kernels, grape seeds, olives, safflowers, sunflowers, copra, corn, coconuts, linseed, hazelnuts, wheat, rice, potatoes, cassavas, legumes, camelina seeds, mustard seeds, and combinations thereof.

As used herein "wet strength" means the measure of how well the web of fibers holding the paper together can resist a force of rupture when the paper is wet. The wet strength may be measured using a Finch Wet Strength Device from Thwing-Albert Instrument Company (West Berlin, N.J.). Where the wet strength is typically effected by wet strength additives such as kymene, cationic glyoxylated resins, polyamidoamine-epichlorohydrin resins, polyamine-epichlorohydrin resins, including epoxide resins. In embodiments, SFAE coated cellulose based material as disclosed herein effects such wet strength in the absence of such additives.

As used herein "wet" means covered or saturated with water or another liquid.

In embodiments, a process as disclosed herein includes mixing of a saccharide fatty acid ester with an inorganic particles (e.g., clay, talc, calcium carbonate) and applying said mixture to a cellulosic material which can allows said particles to adhere to said cellulosic material, where said process comprises contacting a cellulose-based material with the combination and exposing the contacted cellulose-based material to heat, radiation, a catalyst or a combination thereof for a sufficient time to bind the combination to the cellulose based material. In a related aspect, such radiation may include, but is not limited to UV, IR, visible light, or a combination thereof. In another related aspect, the reaction may be carried out at room temperature (i.e., 25° C.) to about 150° C., about 50° C. to about 100° C., or about 60° C. to about 80° C.

Further, the binding reaction between the mixture and the cellulosic material may be carried out with or substantially reduced retention aids (i.e., binders such as PvOH or starch). In one aspect, the mixture may contain a mixture of mono-, di-, tri-, tetra-, penta-, hexa-, hepta-, or octaesters. In another aspect, the may also may contain proteins, polysaccharides and lipids, including but not limited to, milk proteins (e.g., casein, whey protein and the like), wheat glutens, gelatins, prolamines (e.g., corn zeins), soy protein isolates, starches, modified starches, acetylated polysaccharides, alginates, carrageenans, chitosans, inulins, long chain fatty acids, waxes, and combinations thereof.

In embodiments, cellulosic material may be made lipophobic by the addition of polyvinyl alcohol (PvOH) and/or prolamines. In one aspect, the prolamines include zein, gliadin, hordein, secalin, katirin and avenin. In a related aspect, the prolamine is zein.

In embodiments, no catalysts and no organic carriers (e.g., volatile organic compounds) are required to carry out the binding reaction, including that no build-up of material is contemplated using the method as disclosed. In a related aspect, the reaction time is substantially instantaneous (i.e., less than 1 second). Further, the resulting material exhibits low blocking.

As disclosed herein, fatty acid esters of all saccharides, including mono-, di-saccharides and tri-saccharides, are adaptable for use in connection with this aspect of the present invention. In a related aspect, the saccharide fatty acid ester may be a mono-, di-, tri-, tetra-, penta-, hexa-, hepta-, or octaester, and combinations thereof, including that the fatty acid moieties may be saturated, unsaturated or a combination thereof.

While not being bound by theory, the interaction between the saccharide fatty acid ester and the cellulose-based material may be by ionic, hydrophobic, van der Waals interaction, or covalent bonding, or a combination thereof. In a related aspect, the saccharide fatty acid ester binding to the cellulose-based material may be substantially irreversible (e.g., using an SFAE comprising a combination of saturated and unsaturated fatty acids).

Further, at a sufficient concentration, the binding of the saccharide fatty acid ester alone is enough to make the cellulose-based material hydrophobic: i.e., hydrophobicity is achieved in the absence of the addition of waxes, rosins, resins, diketenes, shellacs, vinyl acetates, PLA, PEI, oils, other water repellant chemicals or combinations thereof (i.e., secondary hydrophobes), including that other properties such as, inter alia, strengthening, stiffening, and bulking of the cellulose-based material is achieved by saccharide fatty acid ester binding alone.

An advantage of the invention as disclosed is that multiple fatty acid chains are reactive with the cellulose, and with the two saccharide molecules in the structure, for example, the sucrose fatty acid esters as disclosed give rise to a stiff crosslinking network, leading to strength improvements in fibrous webs such as paper, paperboard, air-laid and wet-laid non-wovens, and textiles, thus may overcome potential unwanted effects of some fillers (e.g., calcium carbonates and lower bonding and tear strength). This is typically not found in other sizing or hydrophobic treatment chemistries. The saccharide fatty acid esters as disclosed herein also generate/increase wet strength, a property absent when using many other water resistant chemistries.

Another advantage is that the saccharide fatty acid esters as disclosed soften the fibers, increasing the space between them, thus, increasing bulk without substantially increasing weight. In addition, fibers and cellulose-based material modified as disclosed herein, may be repulped. Further, for example, water cannot be easily "pushed" past the low surface energy barrier into the sheet.

Saturated SFAE are typically solids at nominal processing temperatures, whereas unsaturated SFAE are typically liquids. This permits the formation of uniform, stable dispersions of saturated SFAE in aqueous coatings without significant interactions or incompatibilities with other coating components, which are typically hydrophilic. In addition, this dispersion allows for high concentrations of saturated SFAE to be prepared without adversely affecting coating rheology, uniform coating application, or coating performance characteristics. The coating surface will become hydrophobic when the particles of saturated SFAE melt and spread upon heating, drying and consolidation of the coating layer. In embodiments, a method of producing bulky, fibrous structures that retain strength even when exposed to water is disclosed. Generally fibrous slurries that are dried form dense structures that are easily broken down upon exposure to water. Formed fiber products made using the method as disclosed may include paper plates, drink holders (e.g., cups), lids, food trays and packaging that would be light weight, strong, and be resistant to exposure to water and other liquids.

In embodiments, saccharide fatty acid esters may be mixed with polyvinyl alcohol (PvOH) to produce sizing agents for water resistant coatings. As disclosed herein, a synergistic relationship between saccharide fatty acid esters and PvOH has been demonstrated, including that with inorganic mixtures, the amount of PvOH may be reduced. While it is known in the art that PvOH is itself a good film former, and forms strong hydrogen bonds with cellulose, it is not very resistant to water, particularly hot water. In aspects, the use of PvOH helps to emulsify saccharide fatty acid esters into an aqueous coating. In one aspect, PvOH provides a rich source of OH groups for saccharide fatty acid esters to crosslink along the fibers, which increases the strength of paper, for example, particularly wet strength, and water resistance beyond what is possible with PvOH alone. For saturated saccharide fatty acid esters with free hydroxyls on the saccharide, a crosslinking agent such as a dialdehyde (e.g., glyoxal, glutaraldehyde, and the like) may also be used.

In embodiments, the saccharide fatty acid esters comprise or consist essentially of sucrose esters of fatty acids. Many methods are known and available for making or otherwise providing the saccharide fatty acid esters of the present invention, and all such methods are believed to be available for use within the broad scope of the present invention. For example, in certain embodiments it may be preferred that the fatty acid esters are synthesized by esterifying a saccharide with one or more fatty acid moieties obtained from oil seeds including but not limited to, soybean oil, sunflower oil, olive oil, canola oil, peanut oil, and mixtures thereof.

In embodiments, the saccharide fatty acid esters comprise a saccharide moiety, including but not limited to a sucrose moiety, which has been substituted by an ester moiety at one or more of its hydroxyl hydrogens. In a related aspect, disaccharide esters have the structure of Formula I.

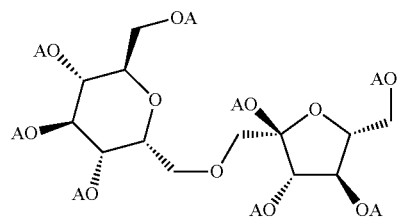

Formula I where "A" is hydrogen or of Structure I below:

Structure I where "R" is a linear, branched, or cyclic, saturated or unsaturated, aliphatic or aromatic moiety of about eight to about 40 carbon atoms, and where at least one "A," is at least one, at least two, at least three, at least four, at least five, at least six, at least seven, and all eight "A" moieties of Formula are in accordance with Structure I. In a related aspect, the saccharide fatty acid esters as described herein may be mono-, di-, tri-, tetra-, penta-, hexa-, hepta-, or octa-esters, and combinations thereof, where the aliphatic groups may be all saturated or may contain saturated and/or unsaturated groups or combinations thereof.

Suitable "R" groups include any form of aliphatic moiety, including those which contain one or more substituents, which may occur on any carbon in the moiety. Also included are aliphatic moieties which include functional groups within the moiety, for example, an ether, ester, thio, amino, phospho, or the like. Also included are oligomer and polymer aliphatic moieties, for example sorbitan, polysorbitan and polyalcohol moieties. Examples of functional groups which may be appended to the aliphatic (or aromatic) moiety comprising the "R" group include, but are not limited to, halogens, alkoxy, hydroxy, amino, ether and ester functional groups. In one aspect, said moieties may have crosslinking functionalities. In another aspect, the SFAE may be crosslinked to a surface (e.g., activated clay/pigment particles). In another aspect, double bonds present on the SFAE may be used to facilitate reactions onto other surfaces.

Suitable disaccharides include raffinose, maltodextrose, galactose, sucrose, combinations of glucose, combinations of fructose, maltose, lactose, combinations of mannose, combinations of erythrose, isomaltose, isomaltulose, trehalose, trehalulose, cellobiose, laminaribiose, chitobiose and combinations thereof.

In embodiments, the substrate for addition of fatty acids may include starches, hemicelluloses, lignins or combinations thereof.

In embodiments, a composition comprises a starch fatty acid ester, where the starch may be derived from any suitable source such as dent corn starch, waxy corn starch, potato starch, wheat starch, rice starch, sago starch, tapioca starch, sorghum starch, sweet potato starch, and mixtures thereof.

In more detail, the starch may be an unmodified starch, or a starch that has been modified by a chemical, physical, or enzymatic modification.

Chemical modification includes any treatment of a starch with a chemical that results in a modified starch (e.g., plastarch material). Within chemical modification are included, but not limited to, depolymerization of a starch, oxidation of a starch, reduction of a starch, etherification of a starch, esterification of a starch, nitrification of a starch, defatting of a starch, hydrophobization of a starch, and the like. Chemically modified starches may also be prepared by using a combination of any of the chemical treatments. Examples of chemically modified starches include the reaction of alkenyl succinic anhydride, particularly octenyl succinic anhydride, with starch to produce a hydrophobic esterified starch; the reaction of 2,3-epoxypropyltrimethylammonium chloride with starch to produce a cationic starch; the reaction of ethylene oxide with starch to produce hydroxyethyl starch; the reaction of hypochlorite with starch to produce an oxidized starch; the reaction of an acid with starch to produce an acid depolymerized starch; defatting of a starch with a solvent such as methanol, ethanol, propanol, methylene chloride, chloroform, carbon tetrachloride, and the like, to produce a defatted starch.

Physically modified starches are any starches that are physically treated in any manner to provide physically modified starches. Within physical modification are included, but not limited to, thermal treatment of the starch in the presence of water, thermal treatment of the starch in the absence of water, fracturing the starch granule by any mechanical means, pressure treatment of starch to melt the starch granules, and the like. Physically modified starches may also be prepared by using a combination of any of the physical treatments. Examples of physically modified starches include the thermal treatment of starch in an aqueous environment to cause the starch granules to swell without granule rupture; the thermal treatment of anhydrous starch granules to cause polymer rearrangement; fragmentation of the starch granules by mechanical disintegration; and pressure treatment of starch granules by means of an extruder to cause melting of the starch granules.

Enzymatically modified starches are any starches that are enzymatically treated in any manner to provide enzymatically modified starches. Within enzymatic modification are included, but not limited to, the reaction of an alpha amylase with starch, the reaction of a protease with starch, the reaction of a lipase with starch, the reaction of a phosphorylase with starch, the reaction of an oxidase with starch, and the like. Enzymatically modified starches may be prepared by using a combination of any of the enzymatic treatments. Examples of enzymatic modification of starch include the reaction of alpha-amylase enzyme with starch to produce a depolymerized starch; the reaction of alpha amylase debranching enzyme with starch to produce a debranched starch; the reaction of a protease enzyme with starch to produce a starch with reduced protein content; the reaction of a lipase enzyme with starch to produce a starch with reduced lipid content; the reaction of a phosphorylase enzyme with starch to produce an enzyme modified phosphated starch; and the reaction of an oxidase enzyme with starch to produce an enzyme oxidized starch.

Disaccharide fatty acid esters may be sucrose fatty acid esters in accordance with Formula I wherein the "R" groups are aliphatic and are linear or branched, saturated or unsaturated and have between about 8 and about 40 carbon atoms.

As used herein the terms "saccharide fatty acid esters" and "sucrose fatty acid ester" include compositions possessing different degrees of purity as well as mixtures of compounds of any purity level. For example, the saccharide fatty acid ester compound can be a substantially pure material, that is, it can comprise a compound having a given number of the "A" groups substituted by only one species of Structure I moiety (that is, all "R" groups are the same and all of the sucrose moieties are substituted to an equal degree). It also includes a composition comprising a blend of two or more saccharide fatty acid ester compounds, which differ in their degrees of substitution, but wherein all of the substituents have the same "R" group structure. It also includes compositions which are a mixture of compounds having differing degrees of "A" group substitution, and wherein the "R" group substituent moieties are independently selected from two or more "R" groups of Structure I. In a related aspect, "R" groups may be the same or may be different, including that said saccharide fatty acid esters in a composition may be the same or may be different (i.e., a mixture of different saccharide fatty acid esters).

For compositions of the present invention, the composition may be comprised of saccharide fatty acid ester compounds having a high degree of substitution. In embodiments, the saccharide fatty acid ester is a sucrose polysoyate.

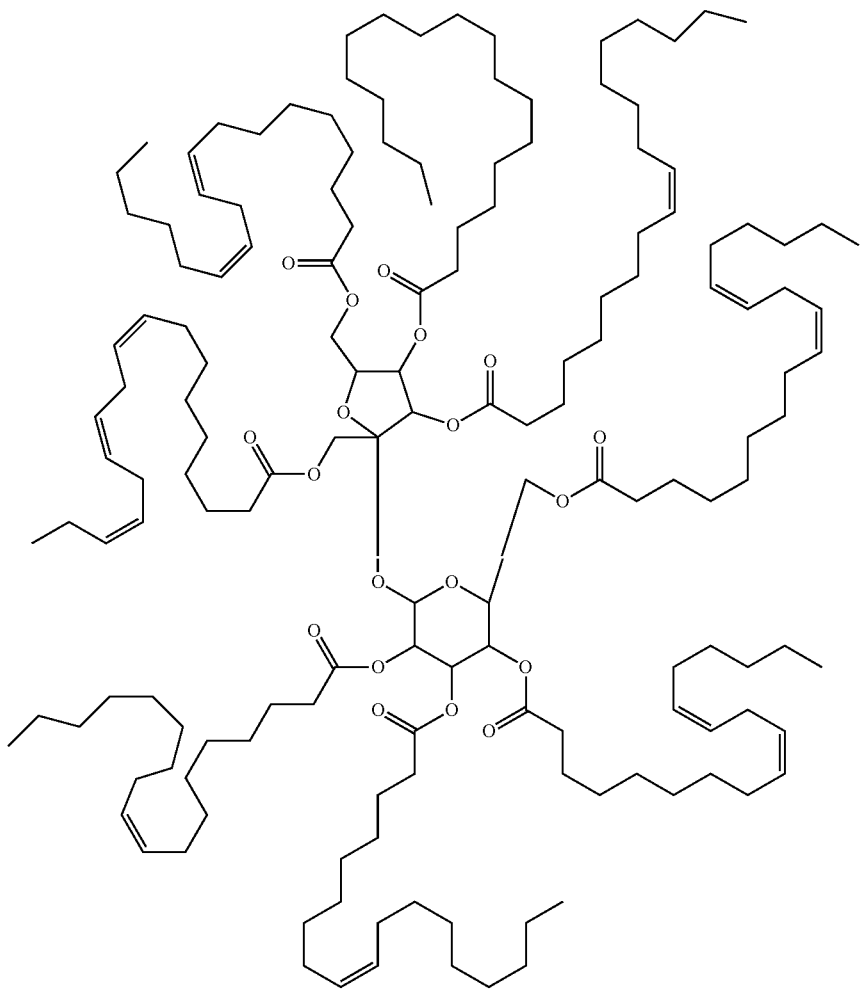

A Sucrose Polysoyate (SEFOSE® 1618U)

Saccharide fatty acid esters may be made by esterification with substantially pure fatty acids by known processes of esterification. They can be prepared also by trans-esterification using saccharide and fatty acid esters in the form of fatty acid glycerides derived, for example, from natural sources, for example, those found in oil extracted from oil seeds, for example soybean oil. Trans-esterification reactions providing sucrose fatty acid esters using fatty acid glycerides are described, for example, in U.S. Pat. Nos. 3,963,699; 4,517,360; 4,518,772; 4,611,055; 5,767,257; 6,504,003; 6,121,440; and 6,995,232, and WO1992004361 A1, herein incorporated by reference in their entireties.

In addition to making hydrophobic sucrose esters via transesterification, similar hydrophobic properties may be achieved in fibrous, cellulosic articles by directly reacting acid chlorides with polyols containing analogous ring structures to sucrose.

As mentioned above, sucrose fatty acid esters may be prepared by trans-esterification of sucrose from methyl ester feedstocks which have been prepared from glycerides derived from natural sources (see, e.g., U.S. Pat. No. 6,995, 232, herein incorporated by reference in its entirety). As a consequence of the source of the fatty acids, the feedstock used to prepare the sucrose fatty acid ester contains a range of saturated and unsaturated fatty acid methyl esters having fatty acid moieties containing between 12 and 40 carbon atoms. This will be reflected in the product sucrose fatty acid esters made from such a source in that the sucrose moieties comprising the product will contain a mixture of ester moiety substituents, wherein, with reference to Structure I above, the "R" groups will be a mixture having between 12 and 26 carbon atoms with a ratio that reflects the feedstock used to prepare the sucrose ester. Further to illustrate this point, sucrose esters derived from soybean oil will be a mixture of species, having "R" group structures which reflect that soybean oil comprises 26 wt. % triglycerides of oleic acid ($H_3C—CH_2]_7—CH=CH—[CH_2]_7—C(O)OH$), 49 wt. % triglycerides of linoleic acid ($H_3—[CH_2]_3—[—CH_2—CH=CH]_2—[—CH_2—]_7—C(O)OH$), 11 wt. % of triglycerides of linolenic acid ($H_3C—[—CH_2—CH=CH—]_3—[CH_2]_7—C(O)OH$), and, 14 wt. % of triglycerides of various saturated fatty acids, as described in the Seventh Ed. Of the Merck Index, which is incorporated herein by reference. All of these fatty acid moieties are represented in the "R" groups of the substituents in the product sucrose fatty acid ester. Accordingly, when referring to a sucrose fatty acid ester herein as the product of a reaction employing a fatty acid feed stock derived from a natural source, for example, sucrose soyate, the term is intended to include all of the various constituents which are typically found as a consequence of the source from which the sucrose fatty acid ester is prepared. In a related aspect, the saccharide fatty acid esters as disclosed may exhibit low viscosity (e.g., between about 10 to 2000 centipoise at room temperature or under standard atmospheric pressure). In another aspect, the unsaturated fatty acids, may have one, two, three or more double bonds.

In embodiments of the present invention, the saccharide fatty acid ester, and in aspects, the disaccharide ester, is formed from fatty acids having greater than about 6 carbon atoms, from about 8 to 16 carbon atoms, from about 8 to about 18 carbon atoms, from about 14 to about 18 carbons atoms, from about 16 to about 18 carbon atoms, from about 16 to about 20 carbon atoms, and from about 20 to about 40 carbon atoms, on average.

In embodiments, the saccharide fatty acid ester may be present in different concentrations to achieve hydrophobicity/lipophobicity depending on the form of the cellulose-based material. In one aspect, when a saccharide fatty acid ester (SFAE) is bound as a coating on the cellulose-based material, the SFAE is present at a coating weight of at least about 0.1 g/m$^2$ to about 1.0 g/m$^2$, about 1.0 g/m$^2$ to about 2.0 g/m$^2$, about 2 g/m$^2$ to about 3 g/m$^2$ on a surface of the cellulose-based material. In a related aspect, it may be present from about 3 g/m$^2$ to about 4 g/m$^2$, about 4 g/m$^2$ to about 5 g/m$^2$, about 5 g/m$^2$ to about 10 g/m$^2$, about 10 g/m$^2$ to about 20 g/m$^2$. In another aspect, when the cellulose-based material is a solution containing cellulose fiber, the SFAE is present at a concentration of at least about 0.025% (wt/wt) of the total fiber present. In a related aspect, it may be present at about 0.05% (wt/wt) to about 0.1% (wt/wt), about 0.1% (wt/wt) to about 0.5% (wt/wt), about 0.5% (wt/wt) to about 1.0% (wt/wt), about 1.0% (wt/wt) to about 2.0% (wt/wt), about 2.0% (wt/wt) to about 3.0% (wt/wt), about 3.0% (wt/wt) to about 4.0% (wt/wt), about 4.0% (wt/wt) to about 5.0% (wt/wt), about 5.0% (wt/wt) to about 10% (wt/wt), about 10% (wt/wt) to about 50% (wt/wt) of the total fiber present. In a further related aspect, the amount of SFAE may be equal to the amount of fiber present. In some embodiments, the SFAE may coat the entire outer surface of a cellulose-based material (e.g., coat an entire piece of paper or cellulose-containing article).

In other embodiments, a coating may comprise between about 0.9% to about 1.0%, about 1.0% to about 5.0%, about 5.0 to about 10%, about 10% to about 20%, about 20% to about 30%, about 40% to about 50% saccharide fatty acid ester by weight of the coating (wt/wt). In a related aspect, the coating may contain between about 25% to about 35% saccharide fatty acid ester by weight of the coating (wt/wt).

In embodiments, the cellulose-based material includes, but is not limited to, paper, paperboard, paper sheets, paper pulp, cups, boxes, trays, lids, release papers/liners, compost bags, shopping bags, shipping bags, bacon board, tea bags, insulating material, containers for coffee or tea, pipes and water conduits, food grade disposable cutlery, plates and bottles, screens for TV and mobile devices, clothing (e.g., cotton or cotton blends), bandages, pressure sensitive labels, pressure sensitive tape, feminine products, and medical devices to be used on the body or inside it such as contraceptives, drug delivery devices, container for pharmaceutical materials (e.g., pills, tablets, suppositories, gels, etc.), and the like. Also, the coating technology as disclosed may be used on furniture and upholstery, outdoors camping equipment and the like.

In one aspect, the coatings as described herein are resistant to pH in the range of between about 3 to about 9. In a related aspect, the pH may be from about 3 to about 4, about 4 to about 5, about 5 to about 7, about 7 to about 9.

In embodiments, an alkanoic acid derivative is mixed with a saccharide fatty acid ester to form an emulsion, where the emulsion is used to treat the cellulose-based material.

In embodiments, the saccharide fatty acid ester may be an emulsifying agent and may comprise a mixture of one or more mono-, di-, tri-, tetra-, penta-, hexa-, hepta-, or octaesters. In another aspect, the fatty acid moiety of the saccharide fatty acid ester may contain saturated groups, unsaturated groups or a combination thereof. In one aspect, the saccharide fatty acid ester-containing emulsion may contain proteins, polysaccharides and/or lipids, including but not limited to, milk proteins (e.g., casein, whey protein and the like), wheat glutens, gelatins, prolamines (e.g., corn zein), soy protein isolates, starches, acetylated polysaccharides, alginates, carrageenans, chitosans, inulins, long chain fatty acids, waxes, and combinations thereof.

In embodiments the saccharide fatty acid ester as disclosed herein may be used in coatings with other chemicals used for paper manufacturing including, but not limited to, agalite, esters, diesters, ethers, ketones, amides, nitriles, aromatics (e.g., xylenes, toluenes), acid halides, anhydrides, alkyl ketene dimer (AKD), alabaster, alganic acid, alum, albarine, glues, barium carbonate, barium sulfate, chlorine dioxide, dolomite, diethylene triamine penta acetate, EDTA, enzymes, formamidine sulfuric acid, guar gum, gypsum, lime, magnesium bisulfate, milk of lime, milk of magnesia, polyvinyl alcohol (PvOH), rosins, rosin soaps, satins, soaps/fatty acids, sodium bisulfate, soda-ash, titania, surfactants, starches, modified starches, hydrocarbon resins, polymers, waxes, polysaccharides, proteins, latex, and combinations thereof. In embodiments, the mixture as disclosed may contain one or more SFAEs and one or more of the following inorganic particles: clay (kaolin, bentonite), calcium carbonate (both GCC and PCC), talc (magnesium silicate), and titanium dioxide. In a related aspect, the inorganic particles may be present at between about 1% to about 2%, about 2% to about 5%, about 5% to about 10%, about 10% to about 20%, about 20% to about 30%, about 30% to about 40%, about 40% to about 50%, about 50% to about 60%, or about 60% to about 70% in a coating composition. In a further related aspect, the SFAEs may be present in an equal, higher or lower proportion compared to the amounts of inorganic particles in a coating. In one aspect, coatings containing one or more SFAEs comprise all saturated fatty acids.

In embodiments, the cellulose-containing material generated by the methods as disclosed herein exhibits greater hydrophobicity or water-resistance relative to the cellulose-containing material without the treatment. In a related aspect, the treated cellulose-containing material exhibits greater lipophobicity or grease resistance relative to the cellulose-containing material without the treatment. In a further related aspect, the treated cellulose-containing material may be biodegradable, compostable, and/or recyclable. In one aspect, the treated cellulose-containing material is hydrophobic (water resistant) and lipophobic (grease resistant).

In embodiments, the treated cellulose-containing material may have improved mechanical properties compared to that same material untreated. For example, paper bags treated by the process as disclosed herein show increased burst strength, Gurley Number, Tensile Strength and/or Energy of Maximum Load. In one aspect, the burst strength is increased by a factor of between about 0.5 to 1.0 fold, between about 1.0 and 1.1 fold, between about 1.1 and 1.3 fold, between about 1.3 to 1.5 fold. In another aspect, the Gurley Number increased by a factor of between about 3 to 4 fold, between about 4 to 5 fold, between about 5 to 6 fold and about 6 to 7 fold. In still another aspect, the Tensile Strain increased by a factor of between about 0.5 to 1.0 fold, between about 1.0 to 1.1 fold, between about 1.1 to 1.2 fold and between about 1.2 to 1.3 fold. And in another aspect, the Energy of Max Load increased by a factor of between about 1.0 to 1.1 fold, between about 1.1 to 1.2 fold, between about 1.2 to 1.3 fold, and between about 1.3 to 1.4 fold.

In embodiments, the cellulose-containing material is a base paper comprising microfibrillated cellulose (MFC) or cellulose nanofiber (CNF) as described for example in U.S. Pub. No. 2015/0167243 (herein incorporated by reference in its entirety), where the MFC or CNF is added during the forming process and paper making process and/or added as a coating or a secondary layer to a prior forming layer to decrease the porosity of said base paper. In a related aspect, the base paper is contacted with the saccharide fatty acid ester as described above. In a further related aspect, the contacted base paper is further contacted with a polyvinyl alcohol (PvOH). In embodiments, the resulting contacted base paper is tuneably water and lipid resistant. In a related aspect, the resulting base paper may exhibit a Gurley value of at least about 10-15 (i.e., Gurley Air Resistance (sec/100 cc, 20 oz. cyl.)), or at least about 100, at least about 200 to about 350. In one aspect, the saccharide fatty acid ester coating may be a laminate for one or more layers or may provide one or more layers as a laminate or may reduce the amount of coating of one or more layers to achieve the same performance effect (e.g., water resistance, grease resistance, and the like). In a related aspect, the laminate may comprise a biodegradable and/or composable heat seal or adhesive.

In embodiments, the saccharide fatty acid esters may be formulated as emulsions, where the choice emulsifying agent and the amount employed is dictated by the nature of the composition and the ability of the agent to facilitate the dispersion of the saccharide fatty acid ester. In one aspect, the emulsifying agents may include, but are not limited to, water, buffers, polyvinyl alcohol (PvOH), carboxymethyl cellulose (CMC), latex, milk proteins, wheat glutens, gelatins, prolamines, soy protein isolates, starches, acetylated polysaccharides, alginates, carrageenans, chitosans, inulins, long chain fatty acids, waxes, agar, alginates, glycerol, gums, lecithins, poloxamers, mono-, di-glycerols, monosodium phosphates, monostearate, propylene glycols, detergents, cetyl alcohol, and combinations thereof. In another aspect, the saccharide ester:emulsifying agent ratios may be from about 0.1:99.9, from about 1:99, from about 10:90, from about 20:80, from about 35:65, from about 40:60, and from about 50:50. It will be apparent to one of skill in the art that ratios may be varied depending on the property(ies) desired for the final product.

In embodiments, the saccharide fatty acid esters may be combined with one or more coating components for internal and surface sizing (alone or in combination), including but not limited to, binders (e.g., starch, soy protein, polymer emulsions, PvOH, latex), and additives (e.g., glyoxal, glyoxalated resins, zirconium salts, calcium stearate, lecithin oleate, polyethylene emulsion, carboxymethyl cellulose, acrylic polymers, alginates, polyacrylate gums, polyacrylates, microbiocides, oil based defoamers, silicone based defoamers, stilbenes, direct dyes and acid dyes). In a related aspect, such components may provide one or more properties, including but not limited to, building a fine porous structure, providing light scattering surface, improving ink receptivity, improving gloss, binding pigment particles, binding coatings to paper, base sheet reinforcement, filling pores in pigment structure, reducing water sensitivity, resisting wet pick in offset printing, preventing blade scratching, improving gloss in supercalendering, reducing dusting, adjusting coating viscosity, providing water holding, dispersing pigments, maintaining coating dispersion, preventing spoilage of coating/coating color, controlling foaming, reducing entrained air and coating craters, increasing whiteness and brightness, and controlling color and shade. It will be apparent to one of skill in the art that combinations may be varied depending on the property(ies) desired for the final product.

In embodiments, the methods employing said saccharide fatty acid esters may be used to lower the cost of applications of primary/secondary coating (e.g., silicone-based layer, starch-based layer, clay-based layer, PLA-layer, Bio-PBS, PEI-layer and the like) by providing a layer of material that exhibits a necessary property (e.g., water resistance, low surface energy, and the like), thereby reducing the amount of primary/secondary layer necessary to achieve that same property. In one aspect, materials may be coated on top of an SFAE layer (e.g., heat sealable agents). In embodiments, the composition is fluorocarbon and silicone free.

In embodiments, the compositions increase both mechanical and thermal stability of the treated product. In one aspect, the surface treatment is thermostable at temperatures between about −100° C. to about 300° C. In further related aspect, the surface of the cellulose-based material exhibits a water contact angle of between about 60° to about 120°. In another related aspect, the surface treatment is chemically stable at temperatures of between about 200° C. to about 300° C.

The substrate which may be dried prior to application (e.g., at about 80-150° C.), may be treated with the modifying composition by dipping, for example, and allowing the surface to be exposed to the composition for less than 1 second. The substrate may be heated to dry the surface, after which the modified material is ready for use. In one aspect, according to the method as disclosed herein the substrate may be treated by any suitable coating/sizing process typically carried out in a paper mill (see, e.g., Smook, G., Surface Treatments in *Handbook for Pulp & Paper Technologists*, (2016), 4th Ed., Cpt. 18, pp. 293-309, TAPPI Press, Peachtree Corners, Ga. USA, herein incorporated by reference in its entirety).

No special preparation of the material is necessary in practicing this invention, although for some applications, the material may be dried before treatment. In embodiments, the methods as disclosed may be used on any cellulose-based surface, including but not limited to, a film, a rigid container, fibers, pulp, a fabric or the like. In one aspect, the saccharide fatty acid esters or coating agents may be applied by conventional size press (vertical, inclined, horizontal), gate roll size press, metering size press, calender size application, tube sizing, on-machine, off-machine, single-sided coater, double-sided coater, short dwell, simultaneous two-side coater, blade or rod coater, gravure coater, gravure printing, flexographic printing, ink-jet printing, laser printing, supercalendering, and combinations thereof.

Depending on the source, the cellulose may be paper, paperboard, pulp, softwood fiber, hardwood fiber, or combinations thereof, nanocellulose, cellulose nanofibres, whiskers or microfibril, microfibrillated, cotton or cotton blends, other non-wood fibers, (such as sisal, jute or hemp, flax and straw) cellulose nanocrystals, or nanofibrilated cellulose.

In embodiments, the amount of saccharide fatty acid ester coating applied is sufficient to completely cover at least one surface of a cellulose-containing material. For example, in embodiments, the saccharide fatty acid ester coating may be applied to the complete outer surface of a container, the complete inner surface of a container, or a combination thereof, or one or both sides of a base paper. In other embodiments, the complete upper surface of a film may be covered by the saccharide fatty acid ester coating, or the complete under surface of a film may be covered by the saccharide fatty acid ester coating, or a combination thereof. In some embodiments, the lumen of a device/instrument may be covered by the coating or the outer surface of the device/instrument may be covered by the saccharide fatty acid ester coating, or a combination thereof. In embodiment, the amount of saccharide fatty acid ester coating applied is sufficient to partially cover at least one surface of a cellulose-containing material. For example, only those surfaces exposed to the ambient atmosphere are covered by the saccharide fatty acid ester coating, or only those surfaces that are not exposed to the ambient atmosphere are covered by the saccharide fatty acid ester coating (e.g., masking). As will be apparent to one of skill in the art, the amount of saccharide fatty acid ester coating applied may be dependent on the use of the material to be covered. In one aspect, one surface may be coated with a saccharide fatty acid ester and the opposing surface may be coated with an agent including, but not limited to, proteins, wheat glutens, gelatins, prolamines, soy protein isolates, starches, modified starches, acetylated polysaccharides, alginates, carrageenans, chitosans, inulins, long chain fatty acids, waxes, and combinations thereof. In a related aspect, the SFAE can be added to a furnish, and the resulting material on the web may be provided with an additional coating of SFAE.

Any suitable coating process may be used to deliver any of the various saccharide fatty acid ester coatings and/or emulsions applied in the course of practicing this aspect of the method. In embodiments, saccharide fatty acid ester coating processes include immersion, spraying, painting, printing, and any combination of any of these processes, alone or with other coating processes adapted for practicing the methods as disclosed.

By increasing the concentration of saccharide fatty acid ester, for example, the composition as disclosed herein may react more extensively with the cellulose being treated with the net result that again improved water-repellent/lipid resistance characteristics are exhibited. However, higher coat weights do not necessarily translate to increased water resistance. In one aspect, various catalysts might allow for speedier "curing" to precisely tune the quantity of saccharide fatty acid ester to meet specific applications.

It will be apparent to one of skill in the art that the selection of cellulose to be treated, the saccharide fatty acid ester, the reaction temperature, and the exposure time are process parameters that may be optimized by routine experimentation to suit any particular application for the final product.

The derivatized materials have altered physical properties which may be defined and measured using appropriate tests known in the art. For hydrophobicity the analytical protocol may include, but is not limited to, the contact angle measurement and moisture pick-up. Other properties include, stiffness, WVTR, porosity, tensile strength, lack of substrate degradation, burst and tear properties. A specific standardized protocol to follow is defined by the American Society for Testing and Materials (protocol ASTM D7334-08).

The permeability of a surface to various gases such as water vapour and oxygen may also be altered by the saccharide fatty acid ester coating process as the barrier function of the material is enhanced. The standard unit measuring permeability is the Barrer and protocols to measure these parameters are also available in the public domain (ASTM std F2476-05 for water vapour and ASTM std F2622-8 for oxygen).

In embodiments, materials treated according to the presently disclosed procedure display a complete biodegradability as measured by the degradation in the environment under microorganismal attack.

Various methods are available to define and test biodegradability including the shake-flask method (ASTM E1279-89 (2008)) and the Zahn-Wellens test (OECD TG 302 B).

Various methods are available to define and test compostability including, but not limited to, ASTM D6400.

Materials suitable for treatment by the process of this invention include various forms of cellulose, such as cotton fibers, plant fibers such as flax, wood fibers, regenerated cellulose (rayon and cellophane), partially alkylated cellulose (cellulose ethers), partially esterified cellulose (acetate rayon), and other modified cellulose materials which have a substantial portion of their surfaces available for reaction/binding. As stated above, the term "cellulose" includes all of these materials and others of similar polysaccharide structure and having similar properties. Among these the relatively novel material microfibrillated cellulose (cellulose nanofiber) (see e.g., U.S. Pat. No. 4,374,702 and US Pub. Nos. 2015/0167243 and 2009/0221812, herein incorporated by reference in their entireties) is particularly suitable for this application. In other embodiments, celluloses may include but are not limited to, cellulose triacetate, cellulose propionate, cellulose acetate propionate, cellulose acetate butyrate, nitrocellulose (cellulose nitrate), cellulose sulfate, celluloid, methylcellulose, ethylcellulose, ethyl methyl cellulose, hydroxyethyl cellulose, hydroxypropyl cellulose, cellulose nanocrystals, hydroxyethyl methyl cellulose, hydroxypropyl methyl cellulose, ethyl hydroxyethyl cellulose, carboxymethyl cellulose, and combinations thereof.

The modification of the cellulose as disclosed herein, in addition to increasing its hydrophobicity, may also increase its tensile strength, flexibility and stiffness, thereby further widening its spectrum of use. All biodegradable and partially biodegradable products made from or by using the modified cellulose disclosed in this application are within the scope of the disclosure, including recyclable and compostable products.

Among the possible applications of the coating technology such items include, but are not limited to, containers for all purpose such as paper, paperboard, paper pulp, cups, lids, boxes, trays, release papers/liners, compost bags, shopping bags, pipes and water conduits, food grade disposable cutlery, plates and bottles, screens for TV and mobile devices, clothing (e.g., cotton or cotton blends), bandages, pressure sensitive labels, pressure sensitive tape, feminine products, and medical devices to be used on the body or inside it such as contraceptives, drug delivery devices, and the like. Also, the coating technology as disclosed may be used on furniture and upholstery, outdoors camping equipment and the like.

The following examples are intended to illustrate but not limit the invention.

EXAMPLES

Example 1. Saccharide Fatty Acid Ester Formulations

SEFOSE® is a liquid at room temperature and all coatings/emulsions containing this material were applied at room temperature using a bench top drawdown device. Rod type and size were varied to create a range of coat weights.
Formulation 1

50 ml of SEFOSE® were added to a solution containing 195 ml of water and 5 grams of carboxymethylcellulose (FINNFIX® 10; CP Kelco, Atlanta, Ga.). This formulation was mixed using a Silverson Homogenizer set to 5000 rpm for 1 minute. This emulsion was coated on a 50 gram base sheet made of bleached hardwood pulp and an 80 gram sheet composed of unbleached softwood. Both papers were placed into an oven (105° C.) for 15 minutes to dry. Upon removal from the oven, sheets were placed on the lab bench and 10 drops of water (room temperature) applied via pipette to each sheet. The base sheets selected for this testing would absorb a droplet of water immediately, whereas sheets coated with varying amounts of SEFOSE® showed increasing levels of water resistance as coat weight increased (see Table 1).

TABLE 1

Base Sheet Results with SEFOSE ®

| Coat weight g/m$^2$ | 50 g Hardwood Base Water Holdout (minutes) | 80 g Softwood Base Holdout (minutes) |
|---|---|---|
| 3.2 | 1 | 0.5 |
| 4.1 | 14 | 9 |
| 6.4 | 30 | 25 |
| 8.5 | 50 | 40 |
| 9.2 | 100+ | 100+ |

It was observed that water resistance was less in the heavier sheet and no water resistance was achieved unless the sheet was dry.
Formulation 2

Addition of SEFOSE® to cup stock: (note this is single layer stock with no MFC treatment. 110 gram board made of Eucalyptus pulp). 50 grams of SEFOSE® was added to 200 grams of 5% cooked ethylated starch (Ethylex 2025) and stirred using a bench top kady mill for 30 seconds. Paper samples were coated and placed in the oven at 105° C. for 15 minutes. 10-15 test droplets were placed on the coated side of the board and water holdout time was measured and recorded in the table below. Water penetration on the untreated board control was instant (see Table 2).

TABLE 2

Penetration of Hot Water for SEFOSE ® Treated Cup Stock

| Quantity Applied g/m$^2$ | Time Required for Hot (80° C.) Water to Penetrate |
|---|---|
| 2.3 | 0.05 hr |
| 4.1 | 0.5 hr |
| 6.2 | 1.2 hr |
| 8.3 | 3.5 hr |
| 9.6 | ~16 hr |

Formulation 3

Pure SEFOSE® was warmed to 45° C. and placed in a spray bottle. A uniform spray was applied to the paper stock listed in the previous example, as well as to a piece of fiberboard and an amount of cotton cloth. When water drops were placed on the samples, penetration into the substrate occurred within 30 seconds, however after drying in the oven for 15 minutes at 105° C. beads of water evaporated before being absorbed into the substrate.

Continued investigation concerned whether SEFOSE® might be compatible with compounds used for oil and grease resistant coatings. SEFOSE® is useful for water resistance as well as stiffness improvements. 240 gram board stock was used to do stiffness tests. Table 3 shows the results. These data were obtained at a single coat weight: 5 grams/square meter with a 5 sample average being reported. Results are in Taber stiffness units recorded with our V-5 Taber stiffness tester Model 150-E.

TABLE 3

Stiffness Test

| Sample tested | Machine Direction Stiffness | Cross Direction Stiffness |
|---|---|---|
| Control board - no coating | 77.6 | 51.8 |
| SEFOSE ® | 85.9 | 57.6 |
| Erucic Acid | 57.9 | 47.4 |
| Palmitoyl chloride | 47.7 | 39.5 |

Example 2. Bonding of Saccharide Ester to Cellulosic Substrate

In an effort to determine whether SEFOSE® was reversibly bound to a cellulosic material, pure SEFOSE® was mixed with pure cellulose at ratio of 50:50. The SEFOSE® was allowed to react for 15 min at 300° F. and the mixture was extracted with methylene chloride (non-polar solvent) or distilled water. The samples were refluxed for 6 hours, and gravimetric analysis of the samples was carried out.

TABLE 4

Extraction of SEFOSE ® from Cellulosic Material

| Sample | Total Mass | SEFOSE ® Mass | SEFOSE ® Extracted | % SEFOSE ® Retained |
|---|---|---|---|---|
| $CH_2Cl_2$ | 2.85 | 1.42 | 0.25 | 83% |
| $H_2O$ | 2.28 | 1.14 | 0.08 | 93% |

Example 3. Examination of Cellulosic Surfaces

Figure 2:
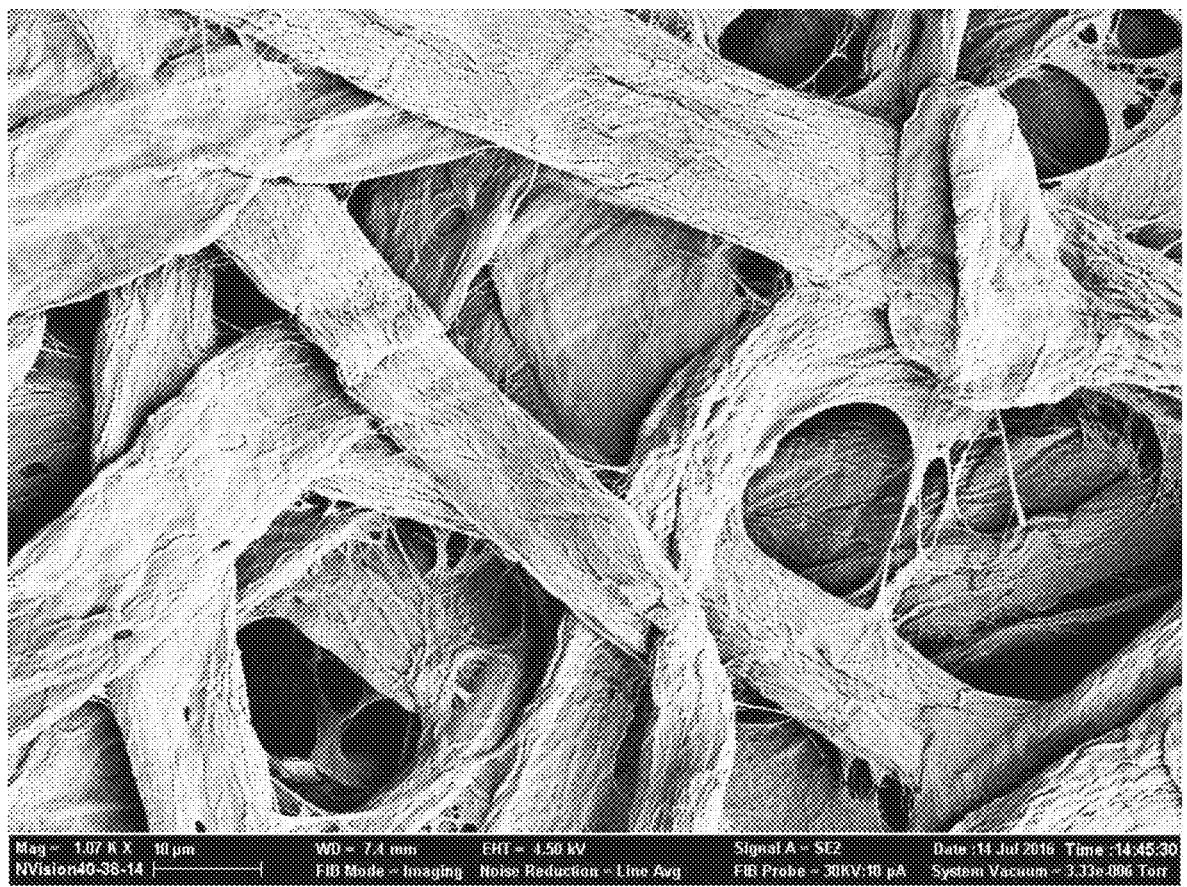
FIG. 2 shows an SEM of untreated, medium porosity Whatman Filter Paper (1070× magnification).
Figure 3:
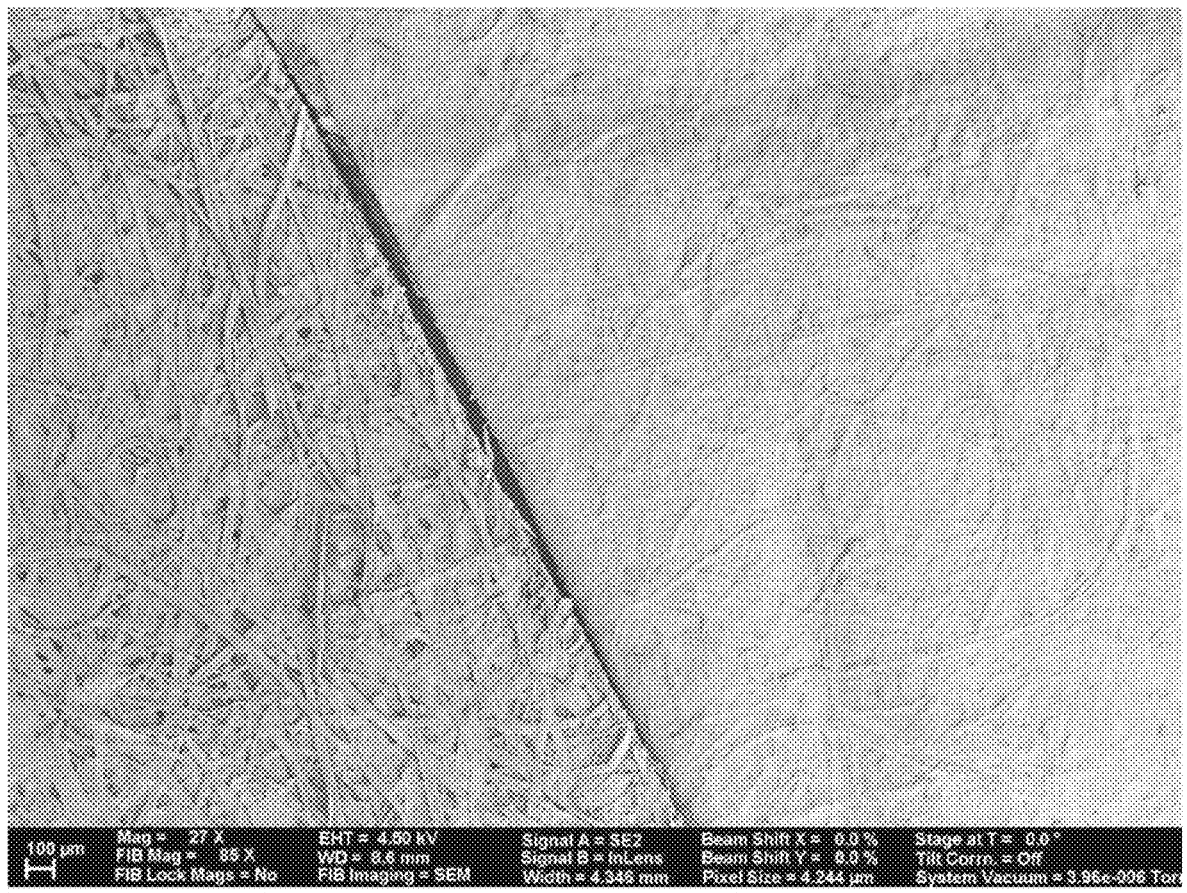
FIG. 3 shows a side-by-side comparison of SEMs of paper made from recycled pulp before (left) and after (right) coating with microfibrillated cellulose (MFC) (27× magnification).
Figure 4:
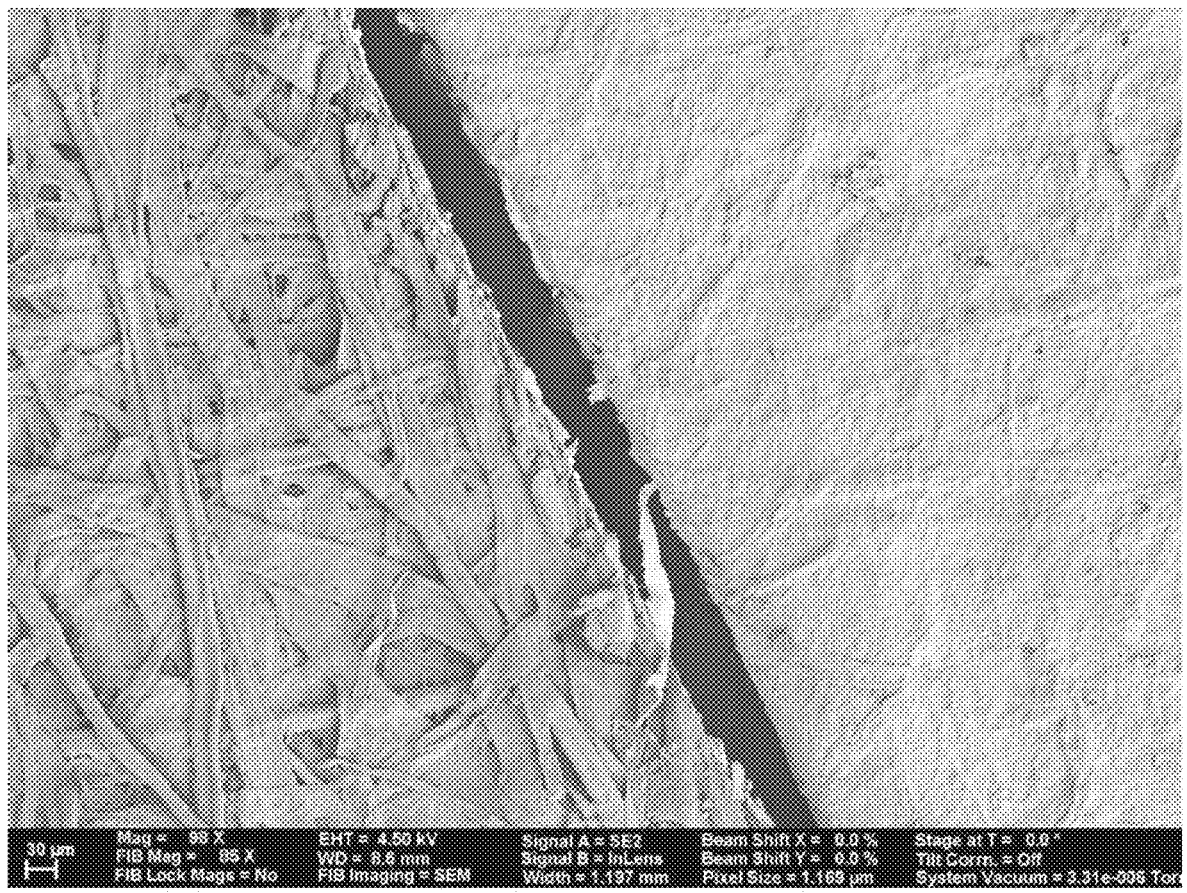
FIG. 4 shows a side-by-side comparison of SEMs of paper made from recycled pulp before (left) and after (right) coating with MFC (98× magnification).

Scanning electron microscope images of base papers with and without MFC illustrate how a less porous base has potential to require far less waterproofing agents reacted to the surface. FIGS. 1-2 show untreated, medium porosity Whatman filter paper. FIGS. 1 and 2 show the relative high surface area exposed for a derivitizing agent to react with; however, it also shows a highly porous sheet with plenty of room for water to escape. FIGS. 3 and 4 show a side by side comparison of paper made with recycled pulp before and after coating with MFC. (They are two magnifications of the same samples, no MCF obviously on the left side of image). The testing shows that derivitization of a much less porous sheet shows more promise for long term water/vapor barrier performance. The last two images are just close ups taken of an average "pore" in a sheet of filter paper as well as a similar magnification of CNF coated paper for contrast purposes.

The data above demonstrate a critical point: that addition of more material results in a corresponding increase in performance. While not being bound by theory, the reaction appears to be faster with unbleached papers, suggesting that the presence of lignin may speed the reaction.

The fact that a product like the SEFOSE® is a liquid, it can readily emulsify, suggesting that it can easily be adapted to work in coating equipment commonly used in paper mills.

Example 4. "Phluphi"

Liquid SEFOSE® was mixed and reacted with bleached hardwood fiber to generate a variety of ways to create a waterproof handsheet. When the sucrose ester was mixed with pulp prior to sheet formation it was found that the majority of it is retained with the fiber. With sufficient heating and drying, a brittle, fluffy but very hydrophobic handsheet was formed. In this example, 0.25 grams SEFOSE® was mixed with 4.0 grams bleached hardwood fiber in 6 Liters of water. This mixture was stirred by hand and the water drained in a standard handsheet mold. The resulting fiber mat was removed and dried for 15 minutes at 325° F. The produced sheet exhibited significant hydrophobicity as well as greatly reduced hydrogen bonding between the fibers themselves. (Water contact angle was observed to be greater than 100 degrees). An emulsifier may be added. SEFOSE® to fiber may be from about 1:100 to 2:1.

Subsequent testing shows that talc is only a spectator in this and was left out of additional testing.

Example 5. Environmental Effects on SEFOSE® Coating Properties

In an effort to better understand the mechanism of sucrose esters reaction with fiber, low viscosity coatings were applied to a bleach kraft sheet that had wet strength resin added, but no water resistance (no sizing). Coatings were all less than 250 cps as measured using a Brookfield Viscometer at 100 rpm.

Figure 5:
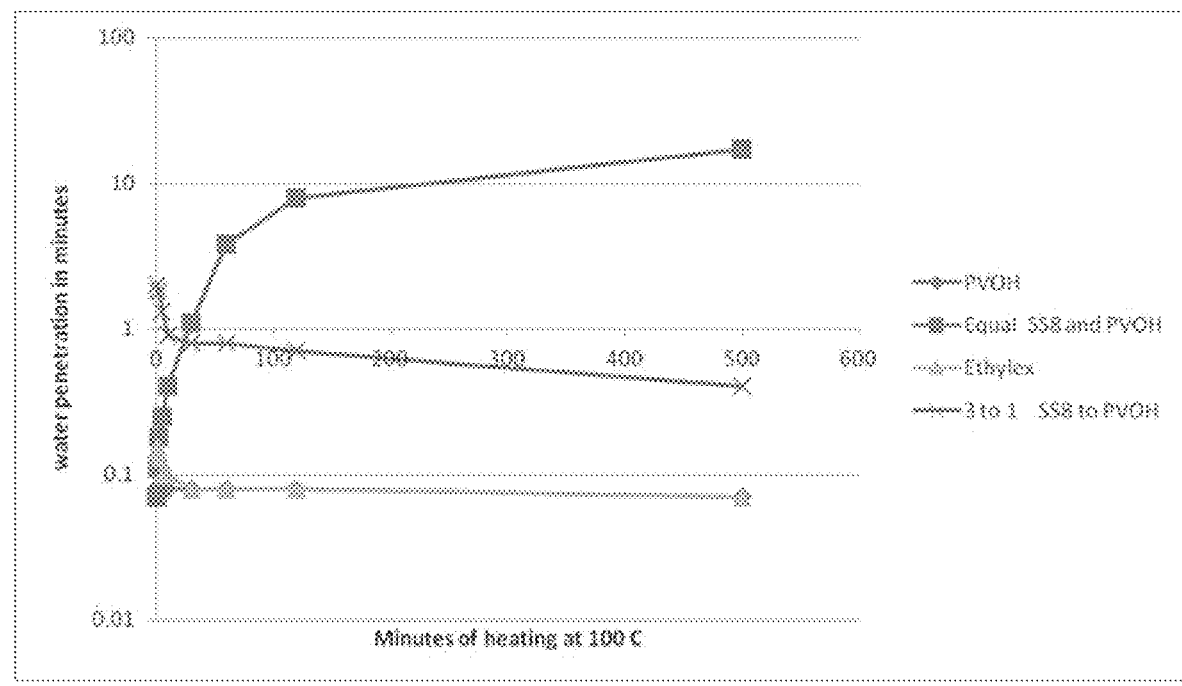
FIG. 5 shows water penetration in paper treated with various coating formulations: polyvinyl alcohol (PvOH), diamonds; SEFOSE®+PvOH at 1:1 (v/v), squares; Ethylex (starch), triangles; SEFOSE®+PvOH at 3:1 (v/v), crosses.

SEFOSE® was emulsified with Ethylex 2025 (starch) and applied to the paper via a gravure roll. For comparison, SEFOSE® was also emulsified with Westcote 9050 PvOH. As shown in FIG. 5, oxidation of the double bonds in SEFOSE® is enhanced by the presence of heat and additional chemical environments that enhance oxidative chemistry (see also, Table 5).

TABLE 5

Environmental Effects on SEFOSE ® (Minutes to Failure)

| Time | PVOH | SEFOSE ®-PVOH | Ethylex | 3:1 |
| --- | --- | --- | --- | --- |
| 0 | 0.08 | 0.07 | 0.15 | 2 |
| 1 | 0.083 | 0.11 | 0.15 | 1.8 |
| 2 | 0.08 | 0.18 | 0.13 | 1.8 |
| 5 | 0.09 | 0.25 | 0.1 | 1.3 |
| 10 | 0.08 | 0.4 | 0.1 | 0.9 |
| 30 | 0.08 | 1.1 | 0.08 | 0.8 |
| 60 | 0.08 | 3.8 | 0.08 | 0.8 |
| 120 | 0.08 | 8 | 0.08 | 0.7 |
| 500 | 0.07 | 17 | 0.07 | 0.4 |

Example 6. Effect of Unsaturated vs. Saturated Fatty Acid Chains

SEFOSE® was reacted with bleached softwood pulp and dried to form a sheet. Subsequently, extractions were carried out with $CH_2Cl_2$, toluene and water to determine the extent of the reaction with pulp. Extractions were performed for at least 6 hours using Soxhlet extraction glassware. Results of the extractions are shown in Table 6.

TABLE 6

Extraction of SEFOSE ®-bound Pulp

|  | Water | $CH_2Cl_2$ | Toluene |
| --- | --- | --- | --- |
| Mass of Dry Pulp | 8.772 g | 9.237 g | 8.090 g |
| SEFOSE ® added | 0.85 g | 0.965 g | 0.798 g |
| Amount Extracted | 0.007 g | 0.015 g | 0.020 g |

The data indicate that essentially all of the SEFOSE® remains in the sheet. To further verify this, the same procedure was carried out on the pulp alone, and results shows that approximately 0.01 g per 10 g of pulp was obtained. While not being bound by theory, this could easily be accounted for as residual pulping chemicals or more likely extractives that had not been completely removed.

Pure fibers of cellulose (e.g., α-cellulose from Sigma Aldrich, St. Louis, Mo.) were used, and the experiment repeated. As long as the loading levels of SEFOSE® remained below about 20% of the mass of the fibers, over 95% of the mass of SEFOSE® was retained with the fibers and not extractable with either polar on non-polar solvents. While not being bound by theory, optimizing baking time and temperature may further enhance the sucrose esters remaining with the fibers.

As shown, the data demonstrate a general inability to extract SEFOSE® out of the material after drying. On the other hand, when the fatty acids containing all saturated fatty acid chains are used instead of SEFOSE® (e.g., OLEAN®, available from Procter & Gamble Chemicals (Cincinnati, Ohio)), nearly 100% of the of the material can be extracted using hot water (at or above 70° C.). OLEAN® is identical to SEFOSE® with the only change being saturated fatty acids attached (OLEAN®) instead of unsaturated fatty acids (SEFOSE®).

Another noteworthy aspect is that multiple fatty acid chains are reactive with the cellulose, and with the two saccharide molecules in the structure, the SEFOSE® gives rise to a stiff crosslinking network leading to strength improvements in fibrous webs such as paper, paperboard, air-laid and wet-laid non-wovens, and textiles.

Example 7. SEFOSE® Additions to Achieve Water Resistance 2 and 3 gram handsheets were made using both hardwood and softwood kraft pulps. When SEFOSE® was added to the 1% pulp slurry at a level of 0.1% or greater and water was drained forming the handsheet, SEFOSE® was retained with the fibers, where it imparted water resistance. From 0.1% to 0.4% SEFOSE®, water beaded on the surface for a few seconds or less. After SEFOSE® loading went above 0.4%, the time of water resistance quickly increased to minutes and then to hours for loading levels greater than 1.5%.

Example 8. Production of Bulky Fibrous Material

Addition of SEFOSE® to pulp acts to soften the fibers, increase space between them increasing bulk. For example, a 3% slurry of hardwood pulp containing 125 g (dry) of pulp was drained, dried and found to occupy 18.2 cubic centimeters volume. 12.5 g of SEFOSE® was added to the same 3% hardwood pulp slurry that contained an equivalent of 125 g dry fiber. Upon draining the water and drying, the resulting mat occupied 45.2 cubic centimeters.

30 g of a standard bleached hardwood kraft pulp (produced by Old Town Fuel and Fiber, LLC, Old Town, Me.) was sprayed with SEFOSE® that had been warmed to 60° C. This 4.3 cm$^3$ was placed in a disintegrator for 10,000 rpm and essentially repulped. The mixture was poured through a handsheet mold and dried at 105° C. The resulting hydrophobic pulp occupied a volume of 8.1 cm$^3$. A 2 inch square of this material was cut and placed in a hydraulic press with 50 tons of pressure applied for 30 seconds. The volume of the square was reduced significantly but still occupied 50% more volume than the same 2 inch square cut for the control with no pressure applied.

It is significant that not only is an increase in bulk and softness observed, but that a forcibly repulped mat when the water was drained resulted in a fiber mat where all of the hydrophobicity was retained. This quality, in addition to the observations that water cannot be easily "pushed" past the low surface energy barrier into the sheet, is of value. Attachment of hydrophobic single-chains of fatty acids do not exhibit this property.

While not being bound by theory, this represent additional evidence that SEFOSE® is reacting with the cellulose and that the OH groups on the surface of the cellulose fibers are no longer available to participate in subsequent hydrogen bonding. Other hydrophobic materials interfere with initial hydrogen bonding, but upon repulping this effect is reversed and the OH groups on the cellulose are free to participate in hydrogen bonding upon redrying.

Example 9. Bag Paper Testing Data

The following table (Table 7) illustrates properties imparted by coating 5-7 g/m$^2$ with a SEFOSE® and polyvinyl alcohol (PvOH) mixture onto an unbleached kraft bag stock (control). Also included for reference are commercial bags.

TABLE 7

Bag Paper Tests

| Paper Type | Caliper (0.001 in) | Tensile (lb/in$^2$) | Burst (psi) |
|---|---|---|---|
| Trial bag (control) | 3.26 | 9.45 | 52.1 |
| Trial bag with SEFOSE ® | 3.32 | 15.21 | 62.6 |
| Sub Sandwich bag | 2.16 | 8.82 | 25.2 |
| Home Depot leaf bag | 5.3 | 17.88 | 71.5 |

As may be seen in the Table, tensile and burst increase with the coating of the control base paper with SEFOSE® and PvOH.

Example 10. Wet/Dry Tensile Strength 3 gram handsheets were made from bleached pulp. The following compares wet and dry tensile strength at different levels of SEFOSE® addition. Note that with these handsheets SEFOSE® was not emulsified into any coating, it was simply mixed into the pulp and drained with no other chemistry added (see Table 8).

TABLE 8

Wet/Dry Tensile Strength

| SEFOSE ® Loading | Wet Strength (lb/in$^2$) | Dry Strength (lb/in$^2$) |
|---|---|---|
| 0% | 0.29 | 9.69 |
| 0.5% | 1.01 | 10.54 |
| 1% | 1.45 | 11.13 |
| 5% | 7.22 | 15.02 |

Note also, that the 5% addition for the wet strength is not far below the dry strength of the control.

Example 11. Use of Esters Containing Less than 8 Saturated Fatty Acids

A number of experiments were carried out with sucrose esters produced having less than 8 fatty acids attached to the sucrose moiety. Samples of SP50, SP10, SP01 and F20W (from Sisterna, The Netherlands) which contain 50, 10, 1 and essentially 0% monoesters, respectively. While these commercially available products are made by reacting sucrose with saturated fatty acids, thus relegating them less useful for further crosslinking or similar chemistries, they have been useful in examining emulsification and water repelling properties.

For example, 10 g of SP01 was mixed with 10 g of glyoxal in a 10% cooked PvOH solution. The mixture was "cooked" at 200° F. for 5 mins and applied via drawdown to a porous base paper made from bleached hardwood kraft. The result was a crosslinked waxy coating on the surface of the paper that exhibited good hydrophobicity. Where a minimum of 3 g/m$^2$ was applied, the resulting contact angle was greater than 100°. Since the glyoxal is a well-known crystallizer used on compounds having OH groups, this method is a potential means to affix fairly unreactive sucrose esters to a surface by bonding leftover alcohol groups on the sucrose ring with an alcohol group made available in the substrate or other coating materials.

Example 12. HST Data and Moisture Uptake

To demonstrate that SEFOSE® alone provides the water proofing properties observed, porous Twins River (Matawaska, Me.) base paper was treated with various amounts of SEFOSE (and PvOH or Ethylex 2025 to emulsify, applied by drawdown) and assayed by Hercules Size Test. The results are shown in Table 9.

TABLE 9

HST Data with SEFOSE ®.

| HST-seconds | SEFOSE ® pickup g/m$^2$ | Emulsifier g/m$^2$ |
|---|---|---|
| <1 | — | — |
| 2.7 | 0 g/m$^2$ | 2.7 g/m$^2$ PvOH |
| 16.8 | 0 g/m$^2$ | 4.5 g/m$^2$ Ethylex 2025 |
| 65 | 2.2 g/m$^2$ | 2.3 g/m$^2$ Ethylex 2025 |
| 389.7 | 1.6 g/m$^2$ | 1.6 g/m$^2$ PvOH |
| 533 | 3.0 g/m$^2$ | 4.0 g/m$^2$ PvOH |
| 1480 | 5.0 g/m$^2$ | 5.0 g/m$^2$ Ethylex 2025 |
| 2300+ | 5.0 g/m$^2$ | 5.0 g/m$^2$ PvOH |

As can be seen in Table 9, increased SEFOSE® applied to the surface of the paper lead to increased water resistance (as shown by increased HST in seconds).

This may also be seen using coatings of a saturated sucrose ester product. For this particular example, the product, F20W (available from Sisterna, The Netherlands) is described as a very low % monoester with most molecules in the 4-8 substitution range. Note that the F20W product pickup is only 50% of the total coating, as it was emulsified with PvOH using equal parts of each to make a stable emulsion. So, where the pickup is labeled "0.5 g/m$^2$" there is also the same pickup of PvOH giving a total pickup of 1.0 g/m$^2$. Results are shown in Table 10.

TABLE 10

HST Data F20W.

| HST-Seconds | Sisterna F20W pickup |
|---|---|
| <1 | 0 |
| 2.0 | 0.5 g/m$^2$ |
| 17.8 | 1.7 g/m$^2$ |
| 175.3 | 2.2 g/m$^2$ |
| 438.8 | 3.5 g/m$^2$ |
| 2412 | 4.1 g/m$^2$ |

As can be seen from Table 10, again, increase F20W increases the water resistance of the porous sheet. Thus, the applied sucrose fatty acid ester itself is making the paper water resistance.

That the water resistance is not simply due to the presence of a fatty acid forming an ester bond with the cellulose, softwood handsheets (bleached softwood kraft) were loaded with SEFOSE® and oleic acid was directly added to the pulp, where the oleic acid forms an ester bond with the cellulose in the pulp. The mass at time zero represents the "bone dry" mass of the handsheets taken out of the oven at 105° C. The samples were placed in a controlled humidity room maintained at 50% RH. The change in mass is noted over time (in minutes). The results are shown in Tables 11 and 12.

TABLE 11

Moisture Uptake SEFOSE ®.

| Time (Min) | 2% SEFOSE ® | 30% SEFOSE ® | Control |
|---|---|---|---|
| 0 | 3.859 | 4.099 | 3.877 |
| 1 | 3.896 | 4.128 | 3.911 |
| 3 | 3.912 | 4.169 | 3.95 |
| 5 | 3.961 | 4.195 | 3.978 |
| 10 | 4.01 | 4.256 | 4.032 |
| 15 | 4.039 | 4.276 | 4.054 |
| 30 | 4.06 | 4.316 | 4.092 |
| 60 | 4.068 | 4.334 | 4.102 |
| 180 | 4.069 | 4.336 | 4.115 |

TABLE 12

Moisture Uptake Oleic Acid.

| Time (hrs) | 30% Oleic Acid | 50% Oleic Acid | Control |
|---|---|---|---|
| 0 | 4.018 | 4.014 | 4.356 |
| 0.5 | 4.067 | 4.052 | 4.48 |
| 2 | 4.117 | 4.077 | 4.609 |
| 3 | 4.128 | 4.08 | 4.631 |
| 5 | 4.136 | 4.081 | 4.647 |
| 21 | 4.142 | 4.083 | 4.661 |

Note the difference here where oleic acid is directly added to the pulp forming an ester bond greatly slows moisture uptake. In contrast, only 2% SEFOSE® slows moisture uptake, at higher concentrations, SEFOSE® does not. As such, while not being bound by theory, the structure of the SEFOSE® bound material cannot be simply explained by the structure formed by simple fatty acid esters and cellulose.

Example 13. Saturated SFAEs

The saturated class of esters are waxy solids at room temperature which, due to saturation, are less reactive with the sample matrix or itself. Using elevated temperatures (e.g., at least 40° C. and for all the ones tested above 65° C.) these material melt and may be applied as a liquid which then cools and solidifies forming a hydrophobic coating. Alternatively, these materials may be emulsified in solid form and applied as an aqueous coating to impart hydrophobic characteristics.

The data shown here represent HST (Hercules Size test) readings obtained from papers coated with varying quantities of saturated SFAEs.

A #45, bleached, hardwood kraft sheet obtained from Turner Falls paper was used for test coatings. The Gurley porosity measured approximately 300 seconds, representing a fairly tight base sheet. S-370 obtained from Mitsubishi Foods (Japan) was emulsified with Xanthan Gum (up to 1% of the mass of saturated SFAE formulation) before coating.

Coat weight of saturated SFAE formulation (pounds per ton) HST (average of 4 measurements per sample).

TABLE 13

| Coat weight of S-370 (pounds per ton) | HST (average of 4 measurements per sample) |
|---|---|
| Control only #0 | 4 seconds |
| #45 | 140 seconds |
| #65 | 385 seconds |
| #100 | 839 seconds |
| #150 | 1044 seconds |
| #200 | 1209 seconds |

Lab data generated also supports that limited amounts of saturated SFAE may enhance water resistance of coatings that are designed for other purposes/applications. For example, saturated SFAE was blended with Ethylex starch and polyvinyl alcohol based coatings and increased water resistance was observed in each case.

The examples below were coated on a #50, bleached recycled base with a Gurley porosity of 18 seconds.

100 grams of Ethylex 2025 were cooked at 10% solids (1 liter volume) and 10 grams of S-370 were added in hot and mixed using a Silverson homogenizer. The resulting coating was applied using a common benchtop drawdown device and the papers were dried under heat lamps.

At 300#/ton coat weight, the starch alone had an average HST of 480 seconds. With the same coat weight of the starch and saturated SFAE mixture, the HST increased to 710 seconds.

Enough polyvinyl alcohol (Selvol 205S) was dissolved in hot water to achieve a 10% solution. This solution was coated on the same #50 paper described above and had an average HST of 225 at 150 pounds/ton of coat weight. Using this same solution, S-370 was added to achieve a mixture in which contained 90% PVOH/10% S-370 on a dry basis (i.e., 90 ml water, 9 grams PvOH, 1 gram S-370): average HST increased to 380 seconds.

Saturated SFAEs are compatible with prolamines (specifically, zein; see U.S. Pat. No. 7,737,200, herein incorporated by reference in its entirety). Since one of the major barriers to commercial production of the subject matter of said patent is that the formulation be water soluble: the addition of saturated SFAEs assists in this manner.

Example 14. Other Saturated SFAEs

Size press evaluations of saturated SFAE based coatings were done on a bleached lightweight sheet (approx. 35 #) that had no sizing and relatively poor formation. All evaluations were done using Exceval HR 3010 PvOH cooked to emulsify the saturated SFAE. Enough saturated SFAE was added to account for 20% of the total solids. The focus was on evaluating the S-370 vs the C-1800 samples (available from Mitsubishi Foods, Japan). Both of these esters performed better than the control, some of the key data are shown in Table 14:

TABLE 14

|  | Average HST | Kit Value |
| --- | --- | --- |
| 10% polyvinyl alcohol alone | 38 sec. | 2 |
| PVOH with S-370 | 85 sec. | 3 |
| PVOH with C-1800 | 82 sec. | 5 |

Note that the saturated compounds appear to give an increase in kit, with both the S-370 and the C-1800 yielding a ~100% increase in HST.

Example 15. Wet Strength Additive

Laboratory testing has shown that the chemistry of the sucrose esters can be tuned to achieve a variety of properties, including use as a wet strength additive. When the sucrose esters are made by attaching saturated groups to each alcohol functionality on the sucrose (or other polyol), the result is a hydrophobic, waxy substance having low miscibility/solubility in water. These compounds may be added to cellulosic materials to impart water resistance either internally or as a coating, however; since they are not chemically reacted to each other or any part of the sample matrix they are susceptible to removal by solvents, heat and pressure.

Where waterproofing and higher levels of water resistance are desired, sucrose esters containing unsaturated functional groups may be made and added to the cellulosic material with the goal of achieving oxidation and/or crosslinking which helps fix the sucrose ester in the matrix and render it highly resistant to removal by physical means. By tuning the number of unsaturated groups as well as the size of the sucrose esters, a means is obtained for crosslinking to impart strength, yet with a molecule that is not optimal for imparting water resistance.

The data shown here is taken by adding SEFOSE® to a bleached kraft sheet at varying levels and obtaining wet tensile data. The percentages shown in the table represent the percent sucrose ester of the treated 70# bleached paper (see Table 15).

TABLE 15

| % SEFOSE ® | Load | Strain/Modulus |
| --- | --- | --- |
| 0% | 4.98 | 0.93/89.04 |
| 1% | 5.12 | 1.88/150.22 |
| 5% | 8.70 | 0.99/345.93 |
| 10% | 10.54 | 1.25/356.99 |
| Dry/untreated | 22.67 | |

The data illustrate a trend in that adding unsaturated sucrose esters to papers increases the wet strength as loading level increases. The dry tensile shows the maximum strength of the sheet as a point of reference.

Example 16. Method of Producing Sucrose Esters Using Acid Chlorides

In addition to making hydrophobic sucrose esters via transesterification, similar hydrophobic properties can be achieved in fibrous articles by directly reacting acid chlorides with polyols containing analogous ring structures to sucrose.

For example, 200 grams of palmitoyl chloride (CAS 112-67-4) were mixed with 50 grams of sucrose and mixed at room temperature. After mixing the mixture was brought to 100° F. and maintained at that temperature overnight (ambient pressure). The resulting material was washed with acetone and deionized water to remove any unreacted or hydrophilic materials. Analysis of remaining material using C-13 NMR showed a significant quantity of hydrophobic sucrose ester had been made.

While it has been shown (by BT3 and others) that the addition of fatty acid chlorides to cellulosic materials could impart hydrophobic properties, the reaction itself is undesirable on site as the by-product given off, gaseous HCl, creates a number of problems including corrosion of surrounding materials and is hazardous to workers and surrounding environment. One additional problem created by the productions of hydrochloric acid is that as more is formed, i.e., more polyol sites are reacted, the weaker the fibrous composition becomes. Palmitoyl chloride was reacted in increasing amounts with cellulose and cotton materials and as hydrophobicity increased, strength of the article decreased.

The reaction above was repeated several times using 200 grams of R—CO-chloride reacted with 50 grams each of other similar polyols, including corn starch, xylan from birch, carboxymethylcellulose, glucose and extracted hemicelluloses.

Example 17. Peel Test

Peel test utilizes a wheel between the two jaws of the tensile tester to measure force needed to peel tape off from a papers surface as a reproducible angle (ASTM D1876; e.g., 100 Series Modular Peel Tester, TestResources, Shakopee, Minn.).

For this work, bleached kraft paper with high Gurley (600 seconds) from Turner Falls paper (Turner's Falls, Mass.) was used. This #50 pound sheet represents a fairly tight, but quite absorbant sheet.

When the #50 pound paper was coated with 15% Ethylex starch as a control, the average force (over 5 samples) that was needed was 0.55 pound/inch. When treated with the same coating but with SEFOSE® substituted for 25% of the Ethylex starch (so 25% pickup is SEFOSE®, 75% is still Ethylex) the average force decreased to 0.081 pounds/inch.

With a 50% substitution of SEFOSE® for the Ethylex, the force needed decreased to less than 0.03 pounds per inch.

The preparation of this paper is in accord with TAPPI standard method 404 for determining tensile strength of papers.

Finally, the same paper was used with S-370 at a loading rate of 750 pounds per ton—which effectively fills all the pours in the sheet creating a complete physical barrier. This indeed passes a TAPPI kit 12 on the flat. This brief experiment shows that it is possible to get grease resistance using saturated SFAE varieties.

Example 18. Saturated SFAE and Inorganic Particles (Fillers)

Saturated sucrose fatty acid esters (SFAE) range from hydrophilic to hydrophobic depending on the number of fatty acid chains (and the chain length) attached to the sucrose molecule. These are not considered to be highly reactive compounds.

A range of substituted SFAEs has been investigated, side chains being 16 or 18 carbons in length. The examined materials are waxy solids with melting points below 150° C. When coated on paper the highly substituted esters impart significant levels of water resistance depending on coat weight and sheet porosity. For this example, the same paper was used with S-370 at a loading rate of 750 pounds per ton—which effectively fills all the pores in the sheet creating a complete physical barrier. The paper treated so was found to possess a TAPPI kit 12. This brief experiment shows that it is possible to get grease resistance using saturated SFAE varieties.

Observations:

More hydrophobic esters tend to aggregate in aqueous emulsions/dispersions and so uniform coatings on the paper become challenging. The low melting point of a number of these molecules results on the coating "melting" into the sheet. If hydrophobic SFAE are mixed with polymers to help stabilize the dispersion, these polymers (i.e., latex, starch, polyvinyl alcohol) tend to surround these esters in a way that mutes the desired hydrophobic properties.

When mixed with calcium carbonate (e.g., precipitated calcium carbonate) there is an attraction which is unexpected. The SFAE does not melt into the paper under the same drying conditions. Calcium carbonate appears to aid in dispersion of the SFAE and adherence is such that the SFAE acts as a binder to attach the calcium carbonate particles to the surface of coated papers. While not being bound by theory, it is thought that this uniform dispersion results in enhanced water resistance for a given amount of ester.

Table 16 shows water resistance as measured by Hercules Size Test (HST) increasing with the formulations containing 50% calcium carbonate. An unsized, porous 40-pound sheet was coated by hand drawdowns. Coat weights were 7-10 g/m$^2$.

TABLE 16

| Coating Composition | HST with 50% PCC (precipitated CaCO$_3$) | HST Without PCC |
| --- | --- | --- |
| Base sheet uncoated | 5 | 4 |
| SFAE alone | 3300 | 1750 |
| SFAE with equal parts polyvinyl alcohol | 1900 | 900 |
| SFAE with equal parts ethylated starch | 1475 | 640 |

The advantages to the combinations as demonstrated include reduced cost of coating via use of carbonate as well as more efficient use of the SFAE molecules as they are more evenly distributed across the surface of the paper substrate.

Example 17. Saturated SFAE Blends and Inorganic Particles (Fillers and Clays)

A. This Example was designed to examine the interaction between saturated sucrose fatty acid ester blends and calcium carbonate.

A paper coating was made having the following composition (on a dry basis): 10% PVOH; 20% sucrose ester (SE-15/1803 blend, SFAEs in equal proportions; SE-15 is available from Hangzhou Union Biotechnology Co., Ltd., Hangzhou China and C-1803 is available from Itochu Chemicals America, Inc., White Plains, N.Y.) and 70% precipitated calcium carbonate (available from OMYA Inc., Blue Ash, Ohio). This mixture was applied to a 65# bleached kraft sheet at a coat weight of 8 g/m$^2$. Calcium carbonate slurry by itself exhibits no water contact angle and no HST when coated on papers. The results using the coating composition are shown in Table 17.

TABLE 17

| Sample | HST (seconds) |
| --- | --- |
| Base Sheet | 0 |
| Base Sheet + CaCO$_3$ | 0 |
| Base Sheet + Sucrose Ester Blend | 35 |
| Base Sheet + CaCO$_3$ + Sucrose Ester Blend | 118 |

This example serves to illustrate that the ester-carbonate interaction is significant enough that the carbonate helps hold the uniformly distributed ester on the surface of the sheet where maximum effect can be observed. Further, the data demonstrates that a bio-based material has been identified that can be used with CaCO$_3$ that results in a coated sheet exhibiting high contact angle when the CaCO$_3$ is present as the majority component of the composition. While not being bound by theory, this effect becomes more apparent when heavy coat weights of a high pigment composition may be applied.

B: This Example was designed to examine the interaction between saturated sucrose fatty acid esters and pigments (e.g., clays).

Kaolin-based materials have very different properties from calcium carbonate. Table 18 shows the results using another SFAE blend, 80 OE (available from Tensac, S.h., Tucuman, Argentina) and SE-15 in equal parts, and 80 OE, SE-15 and Imerys CAPIM™ (kaolin-based material, available from Imerys Clay, Inc., Roswell, Ga.) in equal parts, to produce an OGR coating. The following formulations were prepared at 10% solids and coated at 5 g/m$^2$

TABLE 18

| Composition | Kit |
| --- | --- |
| CAPIM ™ | 0 |
| SE-15 | 3 |
| 80 OE | 3 |
| 80 OE/SE 15 | 4 |
| 80 OE/SE-15/CAPIM ™ | 5/6 |

Once the pigment is present above 10-20%, using CAPIM™ alone the paper exhibits no kit, and as stated above, once the concentration is above 10 or 20% pigment in any barrier coating, typically barrier properties are significantly reduced (e.g., grease is able to find pores to penetrate). The observation that esters give better grease resistance with less net ester in the formulation is significant.

Other Uses

Cup base stock was found to be heavily treated with rosin to increase water resistance. However, the Gurley on this board was found to be 50 seconds indicating a fairly porous board. This material is repulpable and steam quickly penetrates to soften it. Pure SEFOSE® was applied to this board and dried in an oven at 100° C. overnight. The resulting material had a plastic like feel and was completely waterproof. By mass, it was 50% (wt/wt) cellulose/50% (wt/wt) SEFOSE®. The Gurley was too high to measure. Submerging a sample in water for 7 days did not significantly soften the material, however, from greenhouse data it seems to biodegrade in approximately 150 days. Common tapes and glues would not stick to this composite material.

Experiments with saturated SFAE and zein have been carried out, as zein has been shown to impart grease resistance to paper. Stable aqueous dispersions of zein (up to 25% in water) to which saturated SFAE was added from 2 to 5% were generated. Observations demonstrated that saturated SFAE "locks down" zein on paper by imparting water resistance (in addition to grease resistance) to the formulation.

The combination of SFAEs, inorganic particles and bioplastics may be mixed to produce a moldable paper for the design of a biodegradable coffee cup lid. Using wood fiber, and sufficient bioplastic fiber (e.g., polybutylene succinate (Bio-PBS) or polylactic acid (PLA)) along with SFAE, the resulting paper base would be water resistant, where SFAE concentration is optimized to ensure water resistance of the article, and where use of cheaper more common materials, such as regular pulp represents a larger percentage of the mass of the lid. Thus, a relatively small amount (e.g., less than 10%) of the mass of the article would be other materials like bio-polymers, thereby allowing for addition of other additives that may be used to give flexibility, improve tear or stretch properties and the like.

The addition of a calcium carbonate/SFAE mixture allows for the control of the density of the lid.

Although the invention has been described with reference to the above examples, it will be understood that modifications and variations are encompassed within the spirit and scope of the invention. Accordingly, the invention is limited only by the following claims. All references disclosed herein are hereby incorporated by reference in their entireties.

What is claimed:

1. An aqueous composition, comprising:
water;
one or more saccharide fatty acid esters (SFAE); and
inorganic particles,
wherein said one or more SFAE is present in said aqueous composition at a sufficient concentration to cause the inorganic particles to adhere to a cellulose based substrate,
wherein said substrate containing said SFAE-adhered inorganic particles exhibits greater water resistance and/or grease resistance compared to said substrate containing only said inorganic particles alone or only said one or more SFAE alone, and
wherein said aqueous composition does not include casein.

2. The aqueous composition of claim 1, wherein the SFAE comprises all unsaturated fatty acids, all saturated fatty acids or a mixture of saturated and unsaturated fatty acids, and optionally, further comprises one or more binders selected from polyvinyl hydroxide (PvOH) or starch.

3. The aqueous composition of claim 1, wherein said one or more SFAE is a mixture of two or more different SFAEs, and wherein said two or more different SFAEs comprise all saturated fatty acids.

4. The aqueous composition of claim 1, wherein said inorganic particles are selected from the group consisting of clay, ground calcium carbonate, precipitated calcium carbonate, talc, titanium dioxide and combinations thereof, and wherein said inorganic particles comprise at least 1% of the composition on a dry basis (db).

5. The aqueous composition of claim 4, wherein said inorganic particles are calcium carbonate particles, and wherein said substrate containing said SFAE-adhered inorganic particles exhibits water resistance.

6. The aqueous composition of claim 4, wherein said inorganic particles are clay particles, and wherein said substrate containing said SFAE-adhered inorganic particles exhibits grease resistance.

7. The aqueous composition of claim 1, wherein said one or more SFAE contains at least one saccharide and at least one aliphatic group comprising 8 to 30 carbons.

8. The aqueous composition of claim 1, wherein said cellulose based substrate is selected from the group consisting of paper, paperboard, paper pulp, a food storage carton, a food storage bag, a shipping bag, a coffee or tea container, a tea bag, bacon board, diapers, weed-block/barrier fabric or film, mulching film, plant pots, packing beads, bubble wrap, oil absorbent material, laminates, envelops, gift cards, credit cards, gloves, raincoats, OGR paper, a shopping bag, a compost bag, release paper, eating utensil, a hot or cold beverage container, cup, paper towels, plate, a carbonated liquid storage bottle, insulating material, a non-carbonated liquid storage bottle, wrapping food film, a garbage disposal container, a food handling implement, a cup lid, a screw on cup lid of moldable paper, paper straws, a fabric fibre, a water storage and conveying implement, medical use paperboard, release paper, an alcoholic or non-alcoholic drink storage and conveying implement, casing, an electronic good outer screen, an internal or external piece of furniture, a curtain, upholstery, film, box, sheet, tray, pipe, water conduit, pharmaceutical product packaging, clothing, medical device, contraceptive, camping equipment, molded cellulosic fiber material and combinations thereof.

9. A method of treating a cellulosic substrate with said aqueous composition according to claim 1, the method comprising:
a) mixing at least one saccharide fatty acid ester (SFAE) with inorganic particles, water, and optionally one or more binders to form said aqueous composition;
b) applying said aqueous composition to at least one surface of said cellulosic substrate; and
c) curing for a sufficient time to allow said composition to adhere to the at least one surface to obtain at least one treated surface of said cellulosic substrate.

10. The method of claim 9, wherein said at least one treated cellulosic surface is hydrophobic.

11. The method of claim 9, wherein said at least one treated cellulosic surface is lipophobic.

12. The method of claim 9, wherein said at least one SFAE comprises all saturated fatty acids or a mixture of saturated and unsaturated fatty acids.

13. The method of claim 9, wherein said at least one SFAE is a mixture of two or more different SFAEs.

14. The method of claim 9, wherein said inorganic particles are selected from the group consisting of clay, ground calcium carbonate, precipitated calcium carbonate, talc, titanium dioxide and combinations thereof, wherein the inorganic particles are present in the mixture at a concentration of at least about 1% on a dry basis (db).

15. The method of claim 14, wherein the composition further comprises polyvinyl alcohol or starch.

16. The method of claim 14, wherein the calcium carbonate is precipitated calcium carbonate.

17. The method of claim 9, wherein the inorganic particles comprise calcium carbonate, and wherein the calcium carbonate comprises greater than or equal to about 50% of the mixture on a dry basis (db).

18. The method of claim 9, wherein the cellulosic substrate is selected from the group consisting of paper, paperboard, paper pulp, a food storage carton, a food storage bag, a shipping bag, a coffee or tea container, a tea bag, bacon board, diapers, weed-block/barrier fabric or film, mulching film, plant pots, packing beads, bubble wrap, oil absorbent material, laminates, envelops, gift cards, credit cards, gloves, raincoats, OGR paper, a shopping bag, a compost bag, release paper, eating utensil, a hot or cold beverage container, cup, paper towels, plate, a carbonated liquid storage bottle, insulating material, a non-carbonated liquid storage bottle, wrapping food film, a garbage disposal container, a food handling implement, a cup lid, a screw on cup lid of moldable paper, paper straws, a fabric fibre, a water storage and conveying implement, medical use paperboard, release paper, an alcoholic or non-alcoholic drink storage and conveying implement, casing, an electronic good outer screen, an internal or external piece of furniture, a curtain, upholstery, film, box, sheet, tray, pipe, water conduit, pharmaceutical product packaging, clothing, medical device, contraceptive, camping equipment, molded cellulosic fiber material and combinations thereof.

19. The composition of claim 1, wherein at least one of said one or more SFAE has an HLB value greater than 7.

20. The composition of claim 1, wherein at least one of said one or more SFAE has an HLB value of equal to or greater than 9.

21. An article of manufacture, comprising:
a cellulose based substrate; and
a coating on a surface of the cellulose based substrate, the coating containing one or more saccharide fatty acid esters (SFAE), inorganic particles, and optionally, one or more binders,
wherein the cellulose based substrate consists essentially of cellulose,
wherein the inorganic particles are adhered to the surface of the cellulose substrate by the one or more SFAE,
wherein the inorganic particles are present in the coating at a concentration of at least 1% on a dry basis (db),
wherein the coating provides the substrate with increased water resistance and/or grease resistance compared to if the substrate was coated with only the one or more SFAE alone or the inorganic particles alone, and
wherein the coating does not include casein.

22. The article of manufacture of claim 21, wherein the cellulose based substrate is selected from the group consisting of paper, paperboard, paper pulp, a food storage carton, a food storage bag, a shipping bag, a coffee or tea container, a tea bag, bacon board, diapers, weed-block/barrier fabric or film, mulching film, plant pots, packing beads, bubble wrap, oil absorbent material, laminates, envelops, gift cards, credit cards, gloves, raincoats, OGR paper, a shopping bag, a compost bag, release paper, eating utensil, a hot or cold beverage container, cup, paper towels, plate, a carbonated liquid storage bottle, insulating material, a non-carbonated liquid storage bottle, wrapping food film, a garbage disposal container, a food handling implement, a cup lid, a screw on cup lid of moldable paper, paper straws, a fabric fibre, a water storage and conveying implement, medical use paperboard, release paper, an alcoholic or non-alcoholic drink storage and conveying implement, casing, an electronic good outer screen, an internal or external piece of furniture, a curtain, upholstery, film, box, sheet, tray, pipe, water conduit, pharmaceutical product packaging, clothing, medical device, contraceptive, camping equipment, molded cellulosic fiber material and combinations thereof.

* * * * *